United States Patent
Prus et al.

(10) Patent No.: US 11,879,973 B2
(45) Date of Patent: Jan. 23, 2024

(54) ECHO-BASED FOCUSING CORRECTION

(71) Applicant: INSIGHTEC, LTD., Tirat Carmel (IL)

(72) Inventors: Oleg Prus, Haifa (IL); Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 262 days.

(21) Appl. No.: 17/312,145

(22) PCT Filed: Dec. 18, 2019

(86) PCT No.: PCT/IB2019/001340
§ 371 (c)(1),
(2) Date: Jun. 9, 2021

(87) PCT Pub. No.: WO2020/128615
PCT Pub. Date: Jun. 25, 2020

(65) Prior Publication Data
US 2022/0043143 A1    Feb. 10, 2022

Related U.S. Application Data

(60) Provisional application No. 62/781,258, filed on Dec. 18, 2018.

(51) Int. Cl.
*G01S 15/89* (2006.01)
*A61B 8/00* (2006.01)

(52) U.S. Cl.
CPC .............. *G01S 15/892* (2013.01); *A61B 8/54* (2013.01)

(58) Field of Classification Search
CPC .............. G01S 15/892; G01S 7/52039; G01S 7/52049; A61B 8/54; A61B 8/481;
(Continued)

(56) References Cited

U.S. PATENT DOCUMENTS

2019/0308038 A1    10/2019  Prus et al.
2022/0043143 A1*    2/2022  Prus ..................... A61B 8/585
(Continued)

FOREIGN PATENT DOCUMENTS

CN    113316419 A  *  8/2021  ............. A61B 8/481
CN    115135248 A  *  9/2022  ............ A61B 8/0891
(Continued)

OTHER PUBLICATIONS

International Search Report and Written Opinion for International Application No. PCT/IB2019/001340, dated May 8, 2020, 11 pages.

*Primary Examiner* — Daniel Pihulic
(74) *Attorney, Agent, or Firm* — Morgan, Lewis & Bockius LLP

(57) ABSTRACT

Various approaches for focusing an ultrasound transducer include introducing at least one transient acoustic reflector located in proximity to at least one target region; generating multiple sonications to the at least one target region; measuring a reflection signal of each of the sonications off the at least one transient acoustic reflector; selecting the measured reflection signals, and based at least in part on the selected reflection signals, adjusting a parameter value associated with at least one of the transducer elements so as to improve an ultrasound focus at the target region.

24 Claims, 13 Drawing Sheets

(58) Field of Classification Search
CPC ............ A61B 8/585; A61N 2007/0039; A61N 2007/0078; A61N 2007/0095; A61N 7/02
See application file for complete search history.

(56) References Cited

U.S. PATENT DOCUMENTS

2022/0288424 A1* 9/2022 Vortman .................. A61N 7/02
2023/0000466 A1* 1/2023 Levy ........................ A61N 7/02
2023/0000469 A1* 1/2023 Prus ..................... A61B 8/0891

FOREIGN PATENT DOCUMENTS

| CN | 115135381 A | * | 9/2022 | ........... A61B 8/4488 |
| GB | 2515134 A | * | 12/2014 | ....... A61B 17/22004 |
| WO | WO-2018020315 A1 | * | 2/2018 | ........... A61B 8/0808 |
| WO | WO-2020128615 A1 | * | 6/2020 | ............. A61B 8/481 |
| WO | WO-2021123905 A2 | * | 6/2021 | ........... A61B 8/0891 |
| WO | WO-2021123906 A1 | * | 6/2021 | ........... A61B 8/4488 |

* cited by examiner

ECHO-BASED FOCUSING CORRECTION

RELATED APPLICATION

This application is the U.S. national stage application of International (PCT) Patent Application Serial No. PCT/IB2019/001340, filed Dec. 18, 2019, claims the benefit of and priority to U.S. Provisional Patent Application No. 62/781,258, filed Dec. 18, 2018, the entire disclosure of each of which is hereby incorporated by reference.

FIELD OF THE INVENTION

The present invention relates, generally, to systems and methods for ultrasound focusing and, more particularly, to focusing using ultrasound echoes.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

The noninvasive nature of ultrasound surgery is particularly appealing for the treatment of brain tumors. However, the human skull has been a barrier to the clinical realization of ultrasound therapy. Impediments to transcranial ultrasound procedures include strong attenuation and the distortions caused by irregularities in the skull's shape, density, and sound speed, which contribute toward destroying the focus and/or decreasing the ability to spatially register received diagnostic information.

To overcome difficulties associated with the human skull, one conventional approach measures phase shifts resulting from travel of an ultrasound beam through the skull and subsequently adjusts ultrasound parameters to account for the aberrations caused at least in part by the skull. For example, a minimally invasive approach uses receiving probes designed for catheter insertion into the brain to measure the amplitude and phase distortion caused by the skull. Catheter insertions, however, still require surgery, which can be painful and can create a risk of infection.

An alternative, completely noninvasive approach uses X-ray computed tomography (CT) images, rather than receiving probes, to predict the wave distortion caused by the skull. In practice, however, computations of the relative phases alone may too be imprecise to enable high-quality focusing. For example, when ultrasound is focused into the brain to treat a tumor, the skull in the acoustic path may cause aberrations that are not readily ascertainable. In such situations, treatment is typically preceded by a focusing procedure in which an ultrasound focus is generated at or near the target, the quality of the focus is measured (using, e.g., thermal imaging or acoustic radiation force imaging (ARFI)), and experimental feedback is used to adjust the phases of the transducer elements to achieve sufficient focus quality.

The preceding focusing procedure, however, may take a substantial amount of time, which may render it impracticable or, at the least, inconvenient for a patient. In addition, ultrasound energy is inevitably deposited into the tissue surrounding the target during the procedure, thereby potentially damaging healthy tissue. While the effect of pre-therapeutic sonications may be minimized by employing an imaging technique that requires only low acoustic intensity (e.g., ARFI), it is generally desirable to limit the number of sonications prior to treatment.

Another approach to estimating the wave aberrations resulting from the skull involves use of an acoustic reflector (e.g., a small cloud of microbubbles) in the focus zone. By transmitting the ultrasound waves to the microbubbles and receiving reflections therefrom, the amplitudes and/or phases associated with the reflected ultrasound can be determined; based thereon, the transducer parameters (e.g., phase shifts and/or amplitudes) can be adjusted to compensate for the aberrations caused at least in part by the skull. While this approach may effectively improve the focusing properties at the target, the received signals from the acoustic reflector are relatively weak compared to reflection signals from other reflectors (such as the skull). As a result, it may be challenging to accurately extract and analyze the relatively weak reflections from the acoustic reflector, limiting the applicability of this approach.

Accordingly, there is a need for more accurate and reliable ways of creating a high-quality ultrasound focus at the target.

SUMMARY

The present invention provides systems and methods for focusing ultrasound beams, through an inhomogeneous medium, at a target region utilizing one or more transient reflectors (e.g., one or more microbubbles). In various embodiments, the transient acoustic reflector(s) is introduced into the patient's body and reaches proximity to the target region. In one embodiment, multiple sonication locations near (e.g., less than 5 mm away) or at the target region are identified; and the transient reflectors are introduced in proximity to (e.g., less than 5 mm away) each of the identified sonication locations. Subsequently, an ultrasound transducer is activated to sequentially generate a focus at each of the identified sonication locations, and the signals reflected from the transient reflectors associated with each of the sonication locations can be measured by the transducer elements and/or one or more acoustic-signal detectors. Optionally, an initial signal-processing procedure may be implemented to select the measured reflection signals from the transient reflectors (as opposed to the background reflectors such as skull). The initial signal-processing procedure may be based on a comparison of the reflection signals from two consecutive measurements. For example, the two consecutively measured reflection signals may be likely from the transient reflector(s) when there is a relatively significant change therebetween (as the transient reflector(s) generally evolves/dissipates during the period between two measurements). In contrast, the reflection signals from the background reflectors during the period between two measurements are relatively invariant. As used herein, the term "transient reflector" refers to an acoustic reflector that dissipates or evolves with time during sonications and the term "background reflector" refers to an acoustic reflector that does not dissipate or evolve significantly during sonication.

In various embodiments, a signal-selection approach is implemented to select reflection signals from single reflectors based on consistency between the reflection signals. In one embodiment, a consistency function is defined, and the reflection signals are considered to have sufficient consistency only when the value of the consistency function is maximized or exceeds a predetermined threshold. Thereafter, all (or at least some) transient acoustic reflectors whose reflections are determined to have sufficient consistency may be computationally shifted to coincide at a single location, and the amplitudes and/or phases associated with the shifted reflection signals and/or the unshifted reflection signal at the coincident location can be determined. Based thereon, the amplitude and/or phase associated with the transducer element measuring the reflection signals can be computed as an average or a weighted average of the amplitudes and/or phases associated with the shifted reflection signals and/or the unshifted reflection signal at the coincident location. The amplitude and/or phase associated with the transducer element reflects the aberration and transmission of the inhomogeneous tissue from the element to the target area. This procedure can be performed on an element-by-element basis in order to determine the parameter values (e.g., amplitudes and/or phases) of all (or at least some) elements of the ultrasound transducer. Subsequently, the ultrasound transducer elements can be activated based on the determined corresponding amplitudes and/or phases, thereby generating a focus having optimal focusing properties at the target. In addition, in some embodiments, this process can be repeated iteratively to achieve better focusing and stop when focusing quality no longer improves or changes.

In addition, the coincident location of the transient acoustic reflector may optionally be compared against a sonication location estimated using one or more other approaches (e.g., CT images and/or physical model). If a difference is detected, the coincident location may be computationally shifted to coincide with the sonication location estimated using the other approach(es); and the parameter values of the transducer elements may be updated accordingly. Again, the transducer elements may thereupon be activated based on the corresponding updated parameter values to generate an ultrasound focus with optimal focusing properties at the target region. As used herein, the term "focusing" means shaping the acoustic beam to have a desired beam shape in the target. In various embodiments, the desired shape may be a tight spot, a line spot, or a conformal spot confined to the target shape.

Accordingly, in a first aspect, the invention pertains to a system for focusing an ultrasound transducer. In various embodiments, the system comprises an ultrasound transducer comprising a plurality of transducer elements for providing sonications to at least one target region; and a controller configured to (a) cause the transducer to generate a plurality of sonications to the at least one target region; (b) measure a reflection signal of each of the sonications off at least one transient acoustic reflector located in proximity to the at least one target region; (c) select the measured reflection signals, and (d) based at least in part on the selected reflection signals, adjust a parameter value associated with at least one of the transducer elements so as to improve an ultrasound focus at the target region.

In some embodiments, the controller is further configured to repeat (a)-(d) after adjusting at least one parameter value associated with at least one of the transducer elements. The controller may be configured to select reflection signals from two consecutive measurements and compare the selected reflection signals. The comparison may, for example, corresponds to a first processed signal generated by subtracting a first background signal associated with a first set of the consecutive measurements from a first reflection signal associated with the first set the consecutive measurements.

In various embodiments, the controller is further configured to generate a second processed signal by subtracting a second background signal associated with a second set of the consecutive measurements from a second reflection signal associated with the second set the consecutive measurements, and to select the reflection signals based at least in part on an amplitude ratio of the first processed signal and the second processed signal. The controller may be configured to select the subtracted first processed signal upon determining that the ratio exceeds a predetermined threshold value. In various embodiments, the controller is further configured to determine at least one of an amplitude, travel time or a phase associated with the first processed signal and adjust the parameter value associated with the at least one said transducer element based at least in part on the determined amplitude and/or phase and/or travel time.

The controller may be further configured to select at least a portion of each of the measured reflection signals and compare the selected portions of the reflection signals from two consecutive measurements. For example, the controller may be configured to select the (at least a) portion based at least in part on a distance between the at least one of the transducer element and the at least one target region. The controller may be configured to determine at least one of an amplitude or a phase associated with the selected portion of each reflection signal and determine a difference between the amplitudes and/or phases associated with the selected portions of the reflection signals in the two consecutive measurements.

In some embodiments, the controller is further configured to determine a noise level associated with the reflection signals and select the reflection signals based at least in part on the noise level and the difference associated with the selected portions of the reflection signals. The controller may adjust the parameter value associated with the at least one said transducer elements based at least in part on the difference upon determining that the difference of the amplitudes and/or phases associated with the selected portions of the reflection signals exceeds twice the noise level. The measured signals may be pre-processed, e.g., using at least one of a filter or IQ Demodulation.

In various embodiments, each of a plurality of the transient acoustic reflectors is located in proximity to one of a plurality of the target regions, and the controller is further configured to sequentially generate the plurality of sonications to each of the transient acoustic reflectors and measure the reflection signals therefrom and select the reflection signals associated with the plurality of sonications from the plurality of transient acoustic reflectors. The controller may be further configured to determine consistency among the reflection signals, associate the reflection signals having sufficient consistency with the target regions, and upon determining that the reflection signals having sufficient consistency are from a number of the target regions that is below a predetermined threshold value, repeat (a)-(c). For example, the controller may be further configured to select the reflection signals based on consistency therebetween, e.g., using a consistency function. The two reflection signals may be determined to be consistent only when a value of the consistency function is maximized or exceeds a predetermined threshold. For example, the consistency function may satisfy at least one of the equations:

$$f(\vec{r'}) = \left| \frac{\sum_{all\ elements} W \times e^{-i\omega\left(t_1 - t_2 - \frac{dr}{c}\right)}}{\sum_{all\ elements} W} \right|,$$

$$f(\vec{r'}) = \left| \frac{\sum_{all\ elements} W \times e^{-i\left(\varphi_1 - \varphi_2 + \omega\left(\frac{dr}{c}\right)\right)}}{\sum_{all\ elements} W} \right|,$$

where W denotes a weighting factor; $\omega = 2\pi f$, $f$ represents the frequency associated with the two reflection signals; c is the average sound velocity in the target area; $\vec{r_i}$ is the geometrical location of the $i^{th}$ transient reflector; $r' = \vec{r_1} - \vec{r_2}$; $t_i$ is the travel time of the $i^{th}$ transient reflector; $\varphi_1$ and $\varphi_2$ denote the phases associated with the two reflection signals, and $dr = |\vec{r_1}| - |\vec{r_2}|$, $|\vec{r_1}|$ and $|\vec{r_2}|$ are element-dependent variables that denote distances between one of the transducer elements measuring the two reflection signals and the transient acoustic reflectors associated with the two reflection signals, respectively. The controller may be further configured to search for at least one of $\vec{r_1}$ or $\vec{r_2}$ to maximize the consistency function.

The controller may be further configured to determine the consistency between two of the reflection signals from two of the transient acoustic reflectors based at least in part on (i) at least one of travel times or receiving phases associated with the two of the reflection signals and (ii) locations associated with the two of the transient acoustic reflectors. For example, the controller may be configured to computationally shift the location of a first one of the two transient acoustic reflectors to coincide with the location of a second one of the two transient acoustic reflectors, computationally determine at least one of an updated travel time or an updated receiving phase associated with the reflection signal from the shifted location of the first one of the two transient acoustic reflectors, and determine the parameter value associated with the at least one said transducer element based at least in part on (i) the updated travel time or the updated receiving phase and (ii) the travel time or the receiving phase of the reflection signal associated with the second one of the two transient acoustic reflectors. Alternatively or in addition, the controller may be configured to determine the parameter value associated with the at least one of the transducer elements based at least in part on an average of (i) the updated travel time or the updated receiving phase and (ii) the travel time or the receiving phase of the reflection signal associated with the second one of the two transient acoustic reflectors.

The controller may be configured to assign a weighting factor to each of (i) the updated travel time or updated receiving phase and (ii) the travel time or receiving phase based on at least one of (i) an amplitude of the corresponding reflection signal or (ii) consistency of the corresponding reflection signal to other reflection signals, the parameter value associated with the at least one of the transducer elements being determined based at least in part on a weighted average of (i) the updated travel time or the updated receiving phase and (ii) the travel time or the receiving phase of the reflection signal associated with the second one of the two transient acoustic reflectors. The controller may be further configured to determine the consistency between more than two reflection signals using a consistency function, and more than two reflection signals may be measured by at least two different transducer elements. At least one of the reflection signals may originate from at least two transient reflectors.

In some embodiments, the system further comprises an imaging device for acquiring a plurality of images of the at least one target region and/or a non-target region surrounding the target region. The controller may be further configured to estimate a location of the at least one target region based at least in part on the acquired images and a physical model and computationally update the parameter value associated with the at least one of the transducer elements so as to generate the ultrasound focus at the estimated target region.

The system may include an administration device for introducing the at least one transient acoustic reflector to the target. The controller may be further configured to cause the transducer to generate acoustic energy for creating the at least one transient acoustic reflector. The ultrasound focus at the target region may be a tight spot, a line spot or a conformal spot.

In another aspect, the invention relates to a method of focusing an ultrasound transducer. In various embodiments, the method comprises the steps of (a) introducing at least one transient acoustic reflector in proximity to at least one target region, (b) generating a plurality of sonications directed to the at least one target region, (c) measuring a reflection signal of each of the sonications off the at least one transient acoustic reflector, (d) selecting the measured reflection signals, and (e) based at least in part on the selected reflection signals, adjusting a parameter value associated with at least one of the transducer elements so as to improve an ultrasound focus at the target region. The background signal may, for example, be a reflection signal or an average of at least two reflection signals.

In some embodiments, the method further comprises repeating steps (b)-(e) after adjusting at least one parameter value associated with at least one of the transducer elements. Reflection signals may be selected from two consecutive measurements and compared. The comparison may correspond to a first processed signal generated by subtracting a first background signal associated with a first set of the consecutive measurements from a first reflection signal associated with the first set the consecutive measurements. In some embodiments, the method further comprises the steps of generating a second processed signal by subtracting a second background signal associated with a second set of the consecutive measurements from a second reflection signal associated with the second set the consecutive measurements, and selecting the reflection signals based at least in part on an amplitude ratio of the first processed signal and the second processed signal. The subtracted first processed signal may be selected upon determining that the ratio exceeds a predetermined threshold value. The method may further include determining the amplitude, travel time and/or phase associated with the first processed signal and adjusting the parameter value associated with the transducer element(s) based at least in part on the determined amplitude and/or phase and/or travel time.

In some embodiments, the method further comprises the steps of selecting at least a portion of each of the measured reflection signals and comparing the selected portions of the reflection signals from two consecutive measurements. The (at least a) portion may be selected based at least in part on a distance between the at least one of the transducer element and the at least one target region. The method may further comprise determining the amplitude or phase associated with the selected portion of each reflection signal and determining a difference between the amplitudes and/or phases associated with the selected portions of the reflection signals in the two consecutive measurements.

In various embodiments, the method further comprises the steps of determining a noise level associated with the reflection signals and selecting the reflection signals based at least in part on the noise level and the difference associated with the selected portions of the reflection signals. The parameter value associated with the at least one said transducer elements may be adjusted based at least in part on the difference upon determining that the difference of the amplitudes and/or phases associated with the selected portions of the reflection signals exceeds twice the noise level.

The measured signals may be pre-processed, e.g., using a filter, IQ Demodulation, or both. In some embodiments, each of a plurality of transient acoustic reflectors is located in proximity to one of a plurality of the target regions, and the method further comprises sequentially generating the plurality of sonications to each of the transient acoustic reflectors and measure the reflection signals therefrom, and selecting the reflection signals associated with the plurality of sonications from the plurality of transient acoustic reflectors. The method may further comprise determining consistency among the reflection signals, associating the reflection signals having sufficient consistency with the target regions, and upon determining that the reflection signals having sufficient consistency are from a number of the target regions that is below a predetermined threshold value, repeating steps (b)-(d).

The reflection signals may be selected based on consistency therebetween. Consistency between two reflection signals may be determined, for example, using a consistency function, and the two reflection signals may be determined to be consistent only when a value of the consistency function is maximized or exceeds a predetermined threshold. In some embodiments, the consistency function satisfies at least one of the equations:

$$f(\vec{r'}) = \left| \frac{\sum_{\text{all elements}} W \times e^{-i\omega\left(t_1 - t_2 - \frac{dr}{c}\right)}}{\sum_{\text{all elements}} W} \right|,$$

$$f(\vec{r'}) = \left| \frac{\sum_{\text{all elements}} W \times e^{-i\left(\varphi_1 - \varphi_2 + \omega\left(\frac{dr}{c}\right)\right)}}{\sum_{\text{all elements}} W} \right|,$$

where W denotes a weighting factor; $\omega = 2\pi f$, $f$ represents the frequency associated with the two reflection signals; c is the average sound velocity in the target area; $\vec{r_i}$ is the geometrical location of the $i^{th}$ transient reflector; $r' = \vec{r_1} - \vec{r_2}$; $t_i$ is the travel time of the $i^{th}$ transient reflector; $\varphi_1$ and $\varphi_2$ denote the phases associated with the two reflection signals, and $dr \equiv |\vec{r_1}| - |\vec{r_2}|$, $|\vec{r_1}|$ and $|\vec{r_2}|$ are element-dependent variables that denote distances between one of the transducer elements measuring the two reflection signals and the transient acoustic reflectors associated with the two reflection signals, respectively. The method may include searching for at least one of $\vec{r_1}$ or $\vec{r_2}$ to maximize the consistency function.

The consistency between two of the reflection signals may be determined from two of the transient acoustic reflectors based at least in part on (i) at least one of travel times or receiving phases associated with the two of the reflection signals and (ii) locations associated with the two of the transient acoustic reflectors. The method may further include computationally shifting the location of a first one of the two transient acoustic reflectors to coincide with the location of a second one of the two transient acoustic reflectors, computationally determining at least one of an updated travel time or an updated receiving phase associated with the reflection signal from the shifted location of the first one of the two transient acoustic reflectors, and determining the parameter value associated with the at least one said transducer element based at least in part on (i) the updated travel time or the updated receiving phase and (ii) the travel time or the receiving phase of the reflection signal associated with the second one of the two transient acoustic reflectors. The parameter value associated with the transducer element(s) may be determined based at least in part on an average of (i) the updated travel time or the updated receiving phase and (ii) the travel time or the receiving phase of the reflection signal associated with the second one of the two transient acoustic reflectors.

In various embodiments, the method further includes the step of assigning a weighting factor to each of (i) the updated travel time or updated receiving phase and (ii) the travel time or receiving phase based on at least one of (i) an amplitude of the corresponding reflection signal or (ii) consistency of the corresponding reflection signal to other reflection signals, the parameter value associated with the at least one of the transducer elements being determined based at least in part on a weighted average of (i) the updated travel time or the updated receiving phase and (ii) the travel time or the receiving phase of the reflection signal associated with the second one of the two transient acoustic reflectors. Once again, the consistency between more than two reflection signals may be determined using a consistency function. More than two reflection signals may be measured by at least two different transducer elements, and at least one of the reflection signals may originate from at least two transient reflectors.

The method may include acquiring a plurality of images of the at least one target region and/or a non-target region surrounding the target region using an imaging device, and may further include the steps of estimating a location of the at least one target region based at least in part on the acquired images and a physical model and computationally updating the parameter value associated with the at least one of the transducer elements so as to generate the ultrasound focus at the estimated target region. In some embodiments, the method further comprises the step of causing the transducer to generate acoustic energy for creating the at least one transient acoustic reflector. The ultrasound focus at the target region may be a tight spot, a line spot or a conformal spot.

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
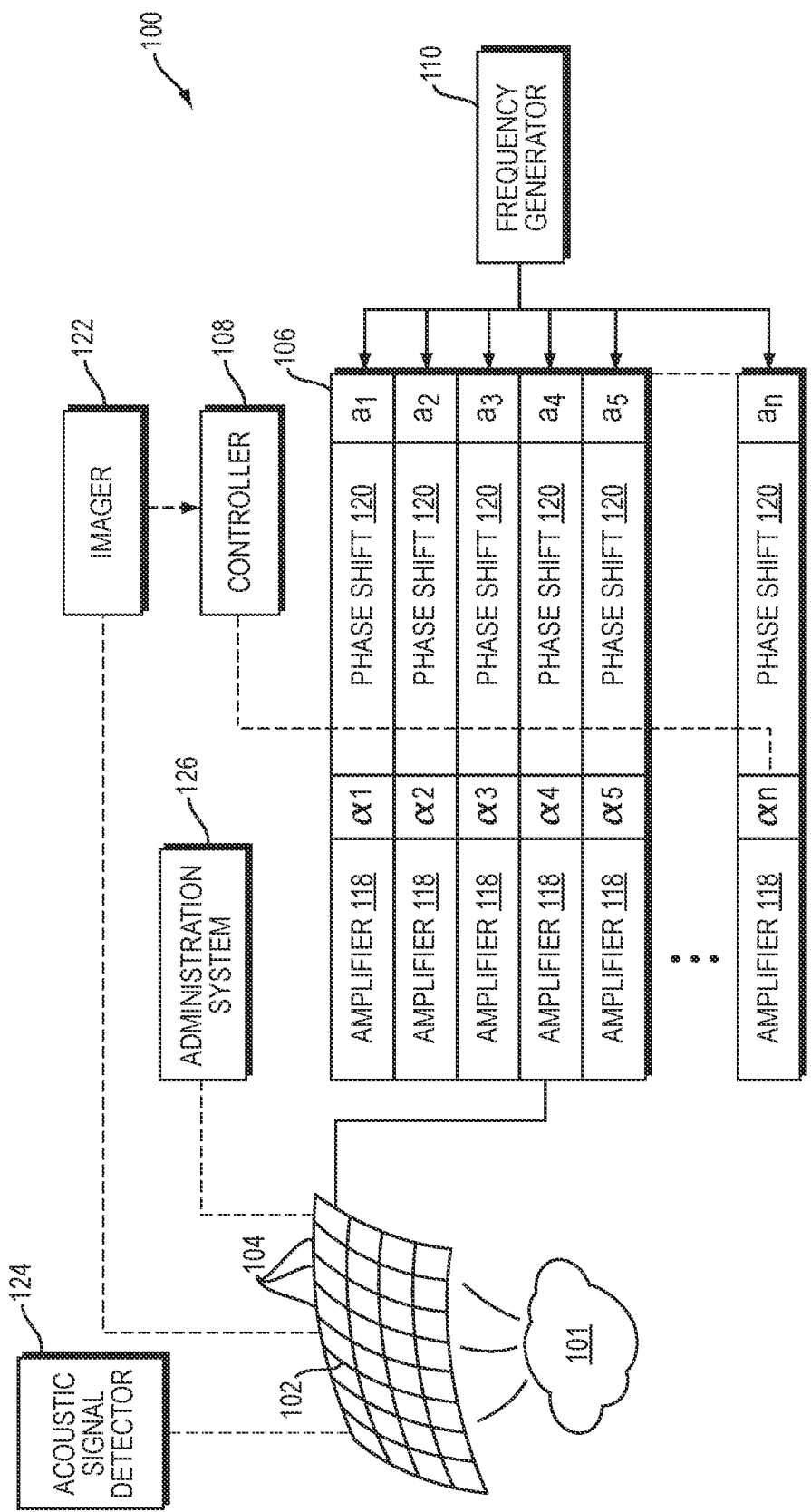
FIG. 1 illustrates a focused ultrasound system in accordance with various embodiments.

FIG. 1 illustrates an exemplary ultrasound system 100 for focusing ultrasound beams through the skull onto a target region 101 within a patient's brain. One of ordinary skill in the art, however, will understand that the ultrasound system 100 described herein may be applied to any part of the human body. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on the surface of the skull or a body part other than the skull, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase delay circuit 120; drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through inhomogeneous tissue (e.g., the patient's skull) onto the target region (e.g., a region in the patient's brain). Via adjustments of the amplification factors and/or the phase shifts, a desired shape and intensity of a focal zone may be created at the target region.

The amplification factors and phase shifts may be computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, to determine the frequency, phase shifts and/or amplification factors of the transducer elements 104. In certain embodiments, the controller computation is based on information about the characteristics (e.g., structure, thickness, density, etc.) of the skull and their effects on propagation of acoustic energy. In various embodiments, such information is obtained from an imager 122, such as a magnetic resonance imaging (MRI) device, a computer tomography (CT) device, a positron emission tomography (PET) device, a singlephoton emission computed tomography (SPECT) device, or an ultrasonography device. The imager 122 may provide a set of two-dimensional images suitable for reconstructing a three-dimensional image of the skull from which thicknesses and densities can be inferred; alternatively, image acquisition may be three-dimensional. In addition, image-manipulation functionality may be implemented in the imager 122, in the controller 108, or in a separate device.

System 100 may be modified in various ways within the scope of the invention. For example, the system may further include an acoustic-signal detector (e.g., a hydrophone) 124 that measures transmitted or reflected ultrasound, and which may provide the signals it receives to the controller 108 for further processing. The reflection and transmission signals may also provide an alternative or additional source for determining the phase shifts and/or amplification factors or feedback for the phase and amplitude adjustments of the beamformer 106 as further described below. The system 100 may contain a positioner for arranging the array 102 of transducer elements 104 with respect to the patient's skull. In order to apply ultrasound therapy to body parts other than the brain, the transducer array 102 may take a different (e.g., cylindrical) shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Figure 2A:
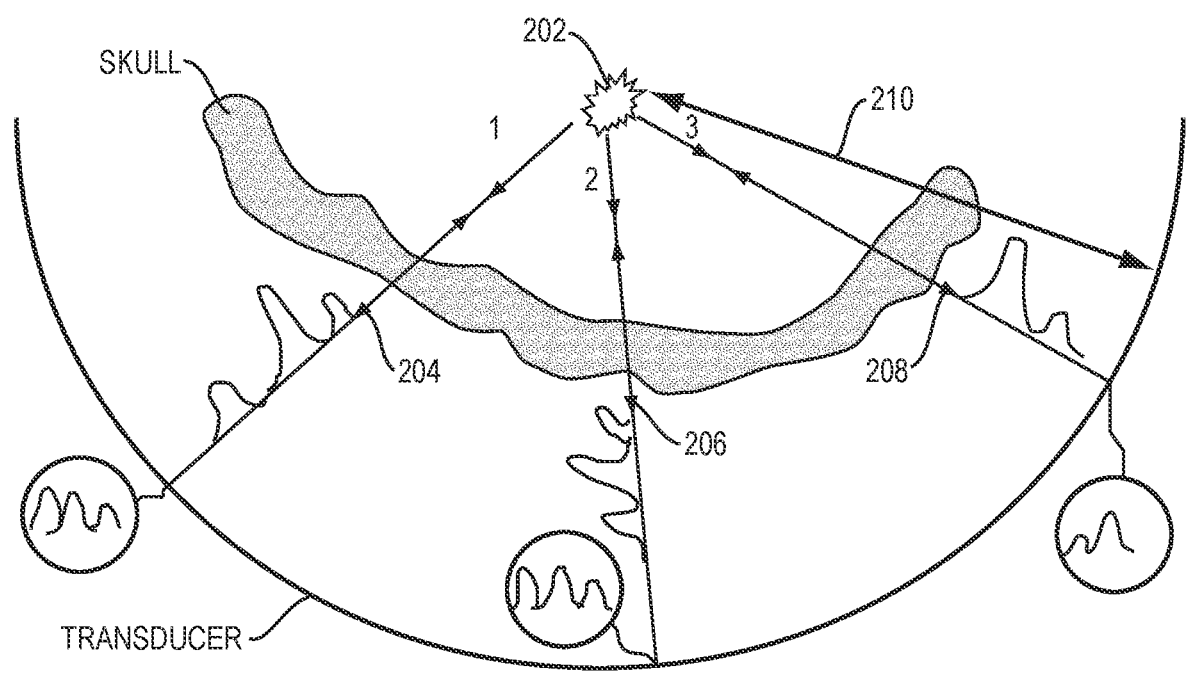
FIG. 2A depicts one or more transient acoustic reflectors located in proximity to one or more target regions in accordance with various embodiments.

In various embodiments, a transient acoustic reflector is introduced into the patient's body intravenously; the transient reflector may either be injected systemically into the patient or locally into the target region 101 using an administration system 126. For example, referring to FIG. 2A, the transient reflector 202 may include or consist of one or more microbubbles introduced into the patient's brain in the form of liquid droplets that subsequently vaporize to form the microbubbles; or as gas-filled bubbles entrained within a liquid carrier, e.g., a conventional ultrasound contrast agent. Alternatively, other substances suitable for cavitation nucleation can be administered instead of bubbles (see, e.g., https://www.springer.com/cda/content/document/cda_downloaddocument/9783642153426-cl.pdf?SGWID=0-0-45-998046-p174031757).

Because of the encapsulated gas, the microbubble(s) 202 may act as reflectors of the ultrasound waves and transmit coherent omnidirectional signals 204-208 to the transducer 102; the reflection signals 204-208 may be substantially concurrently detected by the transducer elements 104 and/or acoustic signal detector 124 associated therewith as further described below. Based on analysis of the reflection signals, the controller 108 may obtain information of the focusing properties at the target region 101 and subsequently adjust the transducer configurations (e.g., phase shifts and/or amplitudes) so as to compensate for the aberrations caused by the intervening tissue 210 located between the transducer elements 104 and target 101, thereby improving the focusing properties at the target region. Approaches to utilizing microbubbles to improve focusing properties of the acoustic beams are provided, for example, in International Application No. PCT/IB2017/000990 (filed on Jul. 19, 2017), the entire content of which is incorporated herein by reference.

Additionally or alternatively, the microbubbles 202 may be generated by applying acoustic energy from the transducer elements 104 to the target 101. The microbubbles 202 can be formed due to the negative pressure produced by the propagating ultrasonic waves or when the heated liquid ruptures and is filled with gas/vapor. In one embodiment, the controller 108 estimates the intensity and/or phase shift of the ultrasound wave emitted from each transducer element 104 using a physical model. For example, using conventional techniques implemented without undue experimentation, the physical model may predict focusing properties (e.g., the shape, size, location and acoustic power of the focus zone) based on information about the geometry of the transducer elements 104 and their locations and orientations relative to the target region 101, as well as the amplitudes and phases of ultrasound waves transmitted from the elements 104. In addition, the physical model may take into account transducer output errors resulting from, for example, transducer elements 104 moving or shifting from their expected locations during manufacturing, use and repair and/or as a result of the elements 104 being deformed by heat. Techniques for determining transducer output errors are provided in U.S. Pat. No. 7,535,794, the contents of which are incorporated herein by reference.

In some embodiments, the physical model further includes parameters, such as material properties of the intervening tissue 210 (e.g., the energy absorption of the tissue or the speed of sound at the employed frequency) along the beam path for predicting the focusing properties at the target 101. Again, the material properties may be collected using the imager 122 as described above and/or other suitable devices. Provided with certain inputs, such as the desired focusing properties, the expected and actual geometries of the transducer elements 104 and their locations and orientations relative to the target region 101, the physical model can compute the required amplitudes and/or phases associated with the transducer elements 104 to produce the focus at the target region 101. In a simplified example, all transducer elements 104 transmit ultrasound waves having a single amplitude value but various phase shifts so as to create a focal intensity above the threshold of forming the microbubbles.

Alternatively, the intensity levels and/or relative phases of the transducer elements 104 may be determined based on transmitted and/or reflected ultrasound measured either prior to or during treatment (e.g., during treatment setup). In addition, these measurements may be utilized to adjust parameters of the physical prediction model. In any case, the estimated intensity levels and/or relative phases of the ultrasound beam may be sufficient to generate the microbubbles 202 in the focal zone that is substantially close to the target region 101, yet without the need to account perfectly for acoustic aberrations caused by inhomogeneous intervening tissue.

In some embodiments, after the transient reflector 202 is generated and/or introduced into the target region 101, the controller 108 may activate at least some of the transducer elements 104 to transmit a series of sonications to the microbubbles located at the target region 101. In one implementation, the transducer elements 104 possess both transmit and detect capabilities. Thus, at least some of the transducer elements 104 may be operated to measure acoustic signals reflected from the target region 101 as described, for example, in International Application No. PCT/IB2019/000644 (filed on Jun. 4, 2019), the contents of which are incorporated herein by reference. Additionally or alternatively, ultrasound reflections from the transient reflector 202 at the target region 101 may be measured using the acoustic-signal detector 124. The measured reflection signals may then be fed to the controller 108 for analysis; based thereon, the controller 108 may adjust the transducer parameters (e.g., amplitudes and/or phases) so as to improve the focusing properties at the target.

Figure 2B:
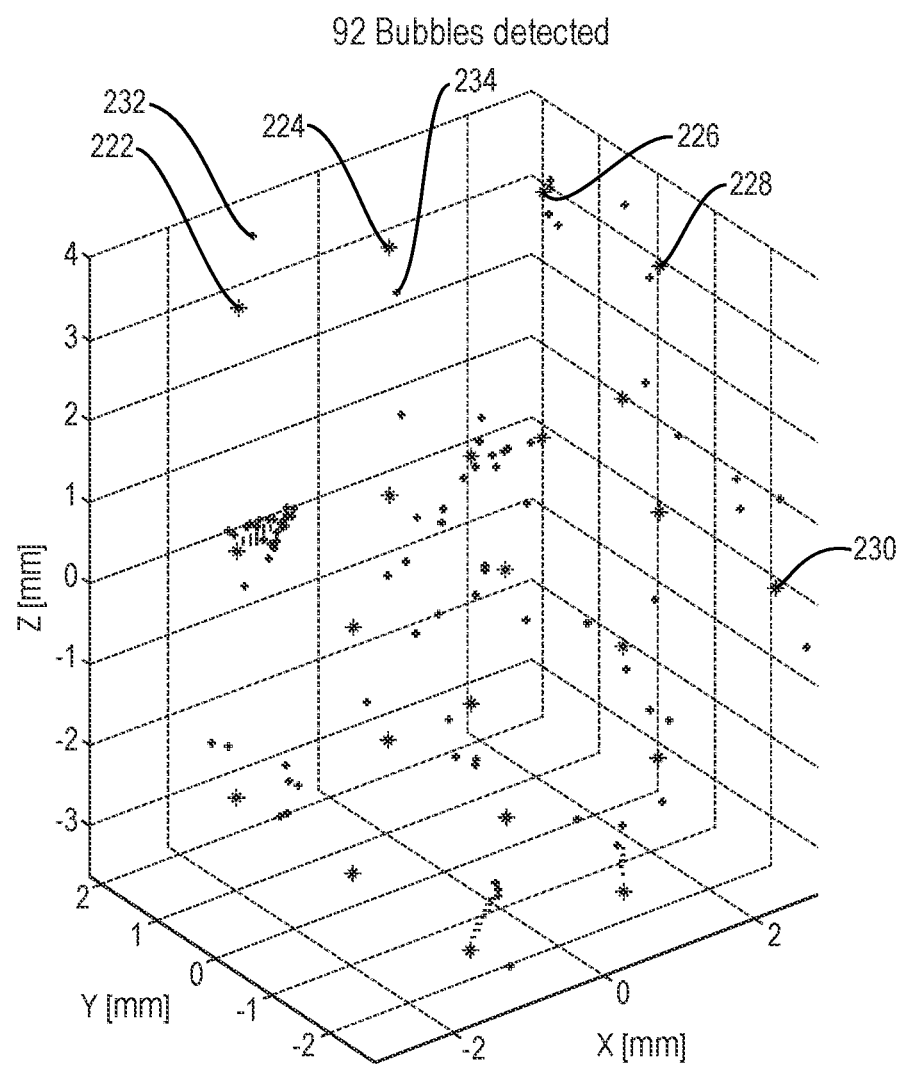
FIG. 2B depicts application of sonications to multiple locations in proximity to a target region in accordance with various embodiments.

The reflection signals from the transient reflector 202, however, may have relatively low quality (e.g., the signal-to-noise ratios (SNRs) are below a threshold); analysis based thereon may therefore result in inaccurate determination of the focusing properties at the target. FIG. 2B illustrates an approach to solving this problem. The ultrasound transducer 102 may be activated to sequentially generate multiple foci at various sonication locations 222-230 that are in proximity to the target region 101 (e.g., less than 5 mm away) or at the target region 101, and each location may have one or more transient reflectors 202 associated therewith. For example, the transducer elements 104 may generate one or more series of sonications to the first sonication location 222 and measure the reflections from the transient reflector 232 located in proximity thereto. Subsequently, the transducer elements 104 may generate another one or more series of sonications to the second sonication location 224 and measure the reflections from the transient reflector 234 associated therewith. This process may continue until a desired number of reflection signals (e.g., at least 10) from the sonication locations in proximity to the target 101 are measured.

In various embodiments, the sonication locations 222-230 are determined based on the image(s) acquired by the imager 122 and/or the ultrasound transducer 102. For example, the imager 122 may acquire images of the target and/or non-target regions: and the ultrasound transducer 102 may acquire images of the transient reflector(s) 202 in the target/non-target regions based on the reflection signals therefrom. Based on the acquired images of the target/non-target regions and the transient reflectors associated therewith, the controller 108 may select the sonication locations 222-230 that are near (e.g., less than 5 mm away) and/or at the target region and having one or more transient reflectors in proximity to thereto (e.g., less than 5 mm away). Approaches to acquiring images of the transient reflector(s) using the reflection signals therefrom are provided, for example, in a U.S. patent application entitled "Systems and Methods for Providing Tissue Information in an Anatomic Target Region Using Reflections from Microbubbles (INS-121PR)" filed on even date herewith, the entire disclosure of which is hereby incorporated by reference.

Figure 3A:
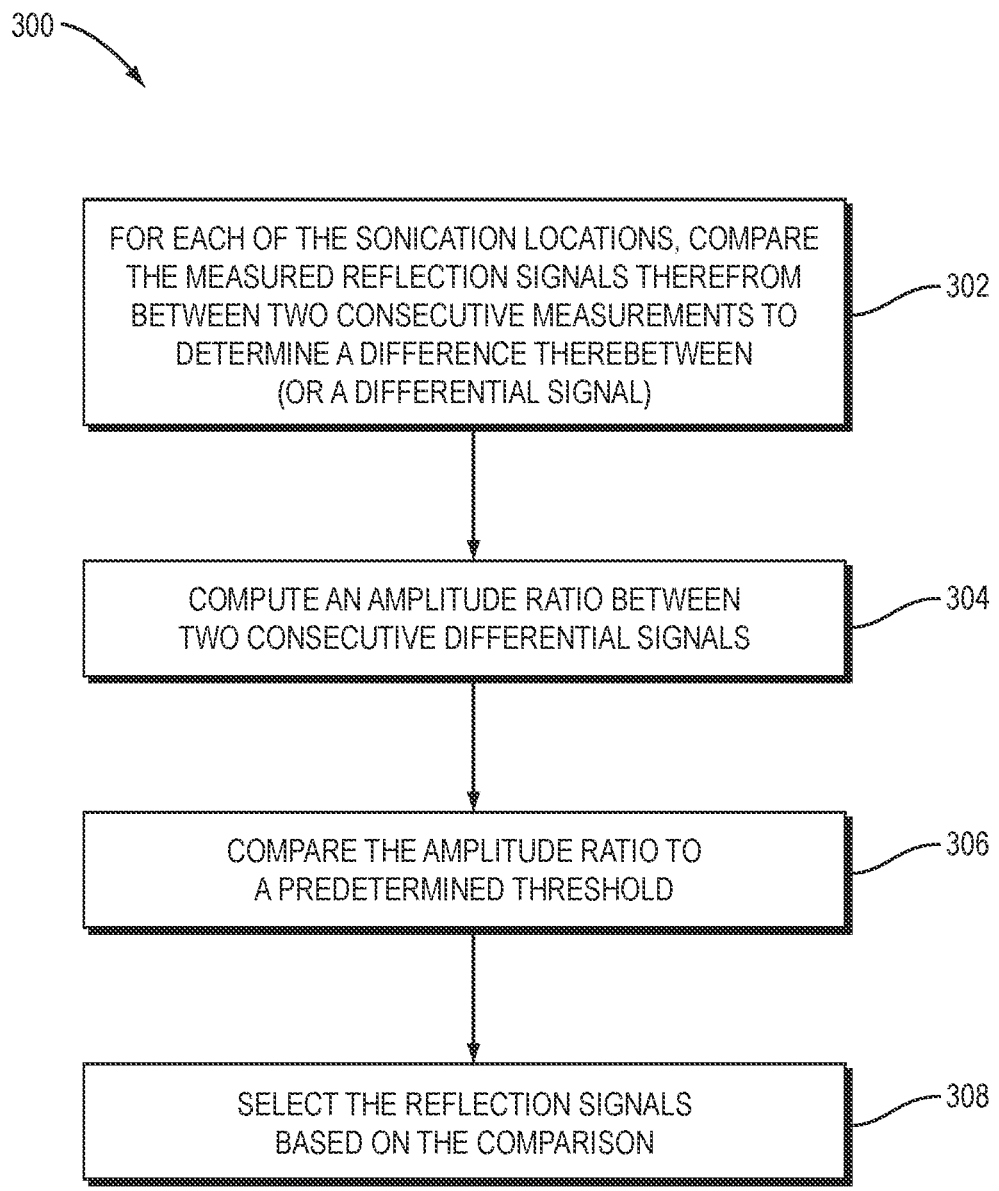
FIG. 3A is a flow chart illustrating an initial signal-processing approach for selecting reflection signals associated with transient reflectors in accordance with various embodiments.
Figure 3B:
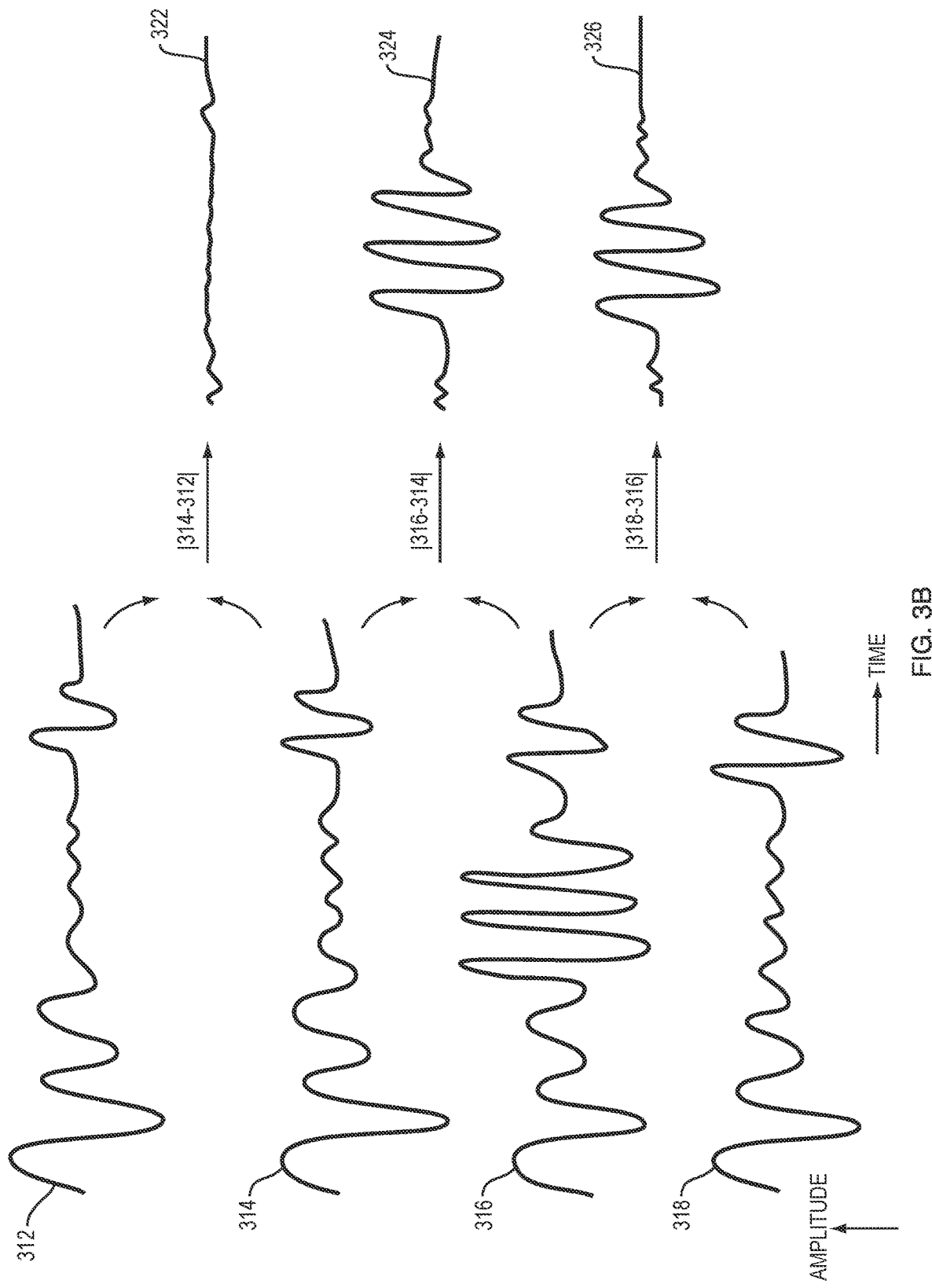
FIG. 3B depicts reflection signals measured from the transient reflectors and differential signals determined based on the measured reflection signals in accordance with various embodiments.

In some embodiments, upon collection of the reflection signals from all (or at least some) of the sonication locations, an initial signal-processing procedure is performed to select signals that are more likely to be from the transient reflectors. This approach may advantageously eliminate (or at least reduce) usage of reflections from the background reflectors (e.g., the skull), thereby improving the accuracy and reliability of the focusing properties determined based on the measured reflection signals. FIG. 3A illustrates an exemplary signal-processing procedure 300 for selecting reflection signals in accordance herewith. In a first step 302, for each of the sonication locations 222-230, the controller 108 compares the measured reflection signals from two consecutive measurements to determine the difference therebetween (or a "differential" signal). For example, FIG. 3B illustrates four reflection signals 312-318 from the first sonication location 222 measured by a transducer element E; the differential signal 322 represents the difference between the reflection signals 314, 312 (obtained, e.g., by subtracting the signal 312 from the signal 314); the differential signal 324 represents the difference between the reflection signals 314, 316; and the differential signal 326 represents the difference between the reflection signals 316, 318. In this example, signals 312, 314, 318 and 320 are essentially background signals and signal 316 is a combination of reflection from transient signals and background signals. Therefore, the difference signals 324 and 326 are approximately a clean reflection from transient reflector signals (up to sign).

Referring again to FIG. 3A, in a second step 304, the controller 108 computes an amplitude ratio between two consecutive differential signals. For example, referring again to FIG. 3B, assuming that the values of the maximal amplitudes associated with the differential signals 322, 324, 326, 328 are 1, 5, 5 and 1, respectively, the amplitude ratio of the differential signal 322 to the differential signal 324 is 0.2, and the amplitude ratio of the differential signal 324 to the differential signal 326 is 1. Referring again to FIG. 3A, the controller 108 then compares the amplitude ratios to a predetermined threshold (e.g., 2) (step 306) and selects reflection signals based on the comparison (step 308). For example, if the amplitude ratio of the differential signal 326 to the differential signal 328 is larger than a predetermined threshold (e.g., 2), the controller 108 selects the differential signal 326 as a reliable signal for further analysis so as to determine the focusing properties at the first sonication location 222. In contrast, since the amplitude ratio of the differential signal 322 to the differential signal 324 is smaller than the predetermined threshold, the signal 322 is discarded.

Implementation of the initial signal-processing approach 300 may advantageously allow the reflection signals from the transient reflectors (e.g., microbubbles), as opposed to the background reflectors, to be selected for further analysis. This is because typically, reflection signals from the background reflectors are relatively invariant between two consecutive measurements, whereas reflection signals from the transient reflectors 202 may exhibit a relatively significant change between two consecutive measurements as the transient reflector evolves/dissipates during the measurement interval. Thus, the differential signals with relatively small amplitude ratios likely originate with the background reflectors; in contrast, large-amplitude reflection signals that have relatively large amplitude ratio may be more likely from the transient reflectors.

Figure 3C:
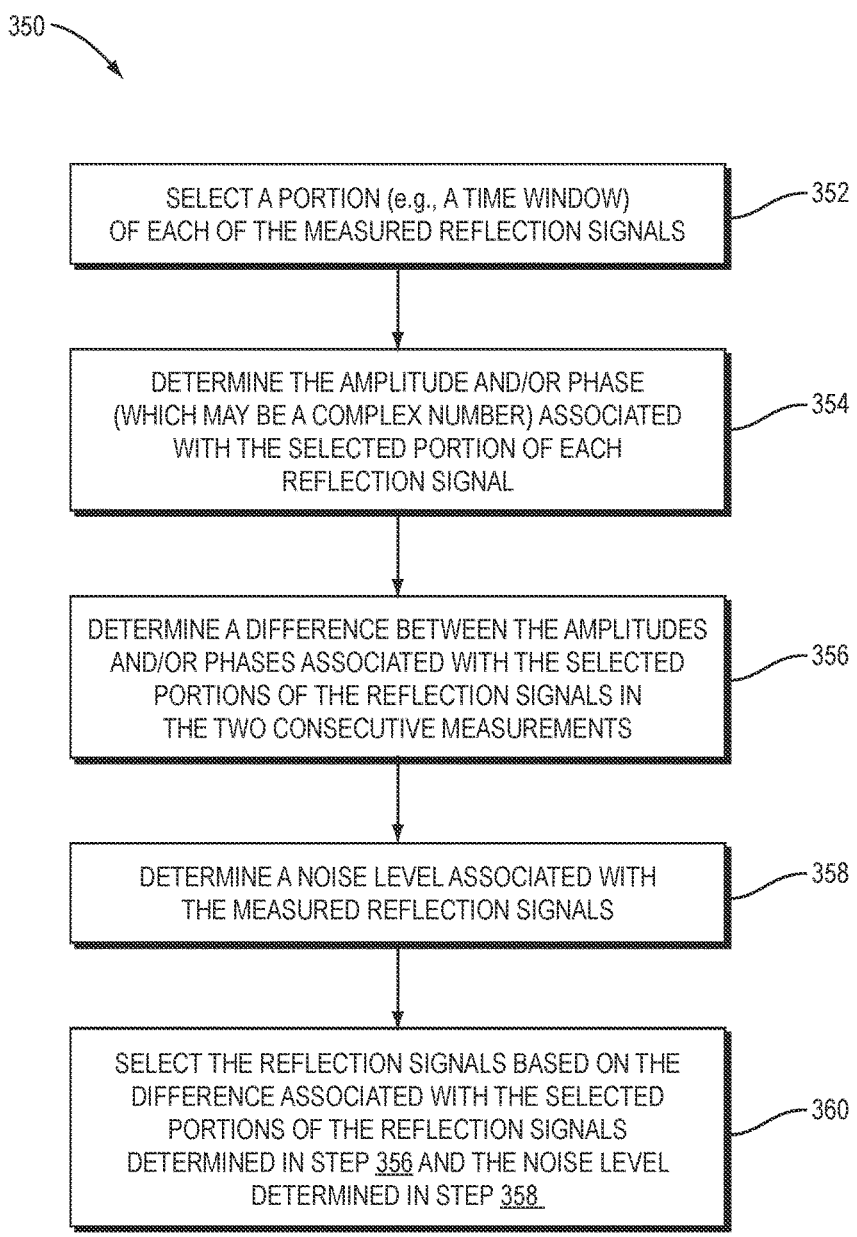
FIG. 3C is a flow chart illustrating another initial signal-processing approach for selecting reflection signals associated with the transient reflectors in accordance with various embodiments.

In practice, the steps of comparing the measured reflection signals to determine the differential signals and determining amplitude ratios between the differential signals may be computationally intensive. To improve SNR and/or reduce the computational time and/or complexity for comparing and selecting the signals, in various embodiments, an alternative initial signal-processing approach 350 can be utilized. Referring to FIG. 3C, in a first step 352, the controller 108 may select a portion (e.g., a time window) of each of the measured reflection signals. In one embodiment, the selection is based on the distance, D, between the transducer element measuring the reflection signal and the sonication location from which the signal is reflected. D may be determined based on the images of the target region 101 acquired using the imager 122 and/or the ultrasound transducer 102. This approach may require registration of the images acquired using two or more imaging systems as described, for example, in U.S. Pat. No. 9,934,570, the entire contents of which are incorporated herein by reference. Once D is determined, the portion (e.g., time window) of the reflection signal corresponding to the transient reflector from which the signal is reflected can be determined based on D and the speed of sound in the tissue. Further details regarding the relationship between the distance, D, the speed of sound and the time window are provided, for example, in U.S. Patent Publication No. 2018/0206816, the entire contents of which are incorporated herein by reference. In some embodiments, the signals (e.g., signals 312, 314) are represented by phase and amplitude as calculated (e.g. by using IQ Demodulation) for the entire signal or the selected portion of the signal.

Figure 3D:
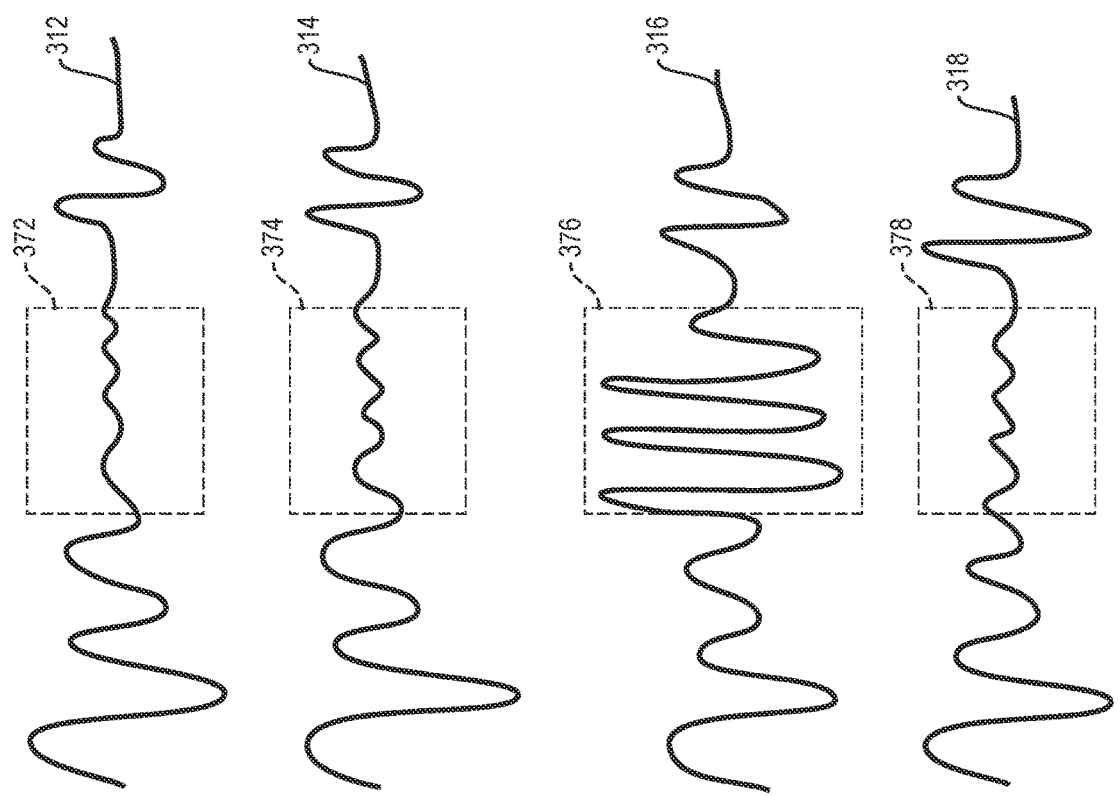
FIG. 3D depicts selections of portions of the measured reflection signals in accordance with various embodiments.

FIG. 3D depicts the portions 372-378 of the measured reflection signals 312-318, respectively, that are selected based on the distance between the transient reflector located in proximity to the first sonication location 222 (since the reflection signals 312-318 are from the first sonication location 222 as described above) and the transducer element E measuring the reflection signals 312-318. In various embodiments, once the portions 372-378 are selected, the controller 108 can determine the amplitude and/or phase (which may be expressed as a complex number) associated with the selected portion of each reflection signal (step 354 in FIG. 3C). Thereafter, the controller 108 may determine the difference between the amplitudes and/or phases associated with the selected portions of the reflection signals in the two consecutive measurements (step 356 in FIG. 3C). For example, the controller 108 may subtract (i) the complex number representing the amplitude and phase associated with the portion 372 from that of the amplitude and phase associated with the portion 374, (ii) the complex number representing the amplitude and phase associated with the portion 374 from that of the amplitude and phase associated with the portion 376, and so on. In addition, the controller 108 may determine a noise level associated with the reflection signals 372-378 (step 358 in FIG. 3C). In various embodiments, the controller 108 then selects the reflection signals based on the difference between the selected portions of the reflection signals determined in step 356 and the noise level determined in step 358 (step 360 in FIG. 3C). For example, referring again to FIG. 3D, the controller 108 may select the reflection signal 316 upon determining that the amplitude and/or phase difference between the selected portions 374, 376 exceeds a predetermined threshold (e.g., twice the noise level). Again, the alternative initial signal-processing approach 350 may advantageously allow the reflection signals from the transient reflectors (e.g., microbubbles), as opposed to the background reflectors, to be selected for further analysis.

Generally, the administration system 126 may introduce a low concentration (e.g., 5% of the concentration used for standard imaging) of microbubbles into the target 101 such that the acoustic reflections are from a point target (e.g., having a size less than that of a quarter of the sonication wavelength) such as a single microbubble (as opposed to a cloud of microbubbles). This is because reflection signals from a cloud of microbubbles may be incoherent and/or exhibit artifacts due to low SNRs and/or vibrations from the multiple microbubbles; as a result, analysis of the reflection signals from the cloud of microbubbles may be inaccurate and adjustment of the transducer parameters based thereon may be insufficient to account for the aberrations caused by the intervening tissue. In addition, analysis of the reflection signals from the cloud of microbubbles may be computationally expensive and time-consuming.

Figure 4A:
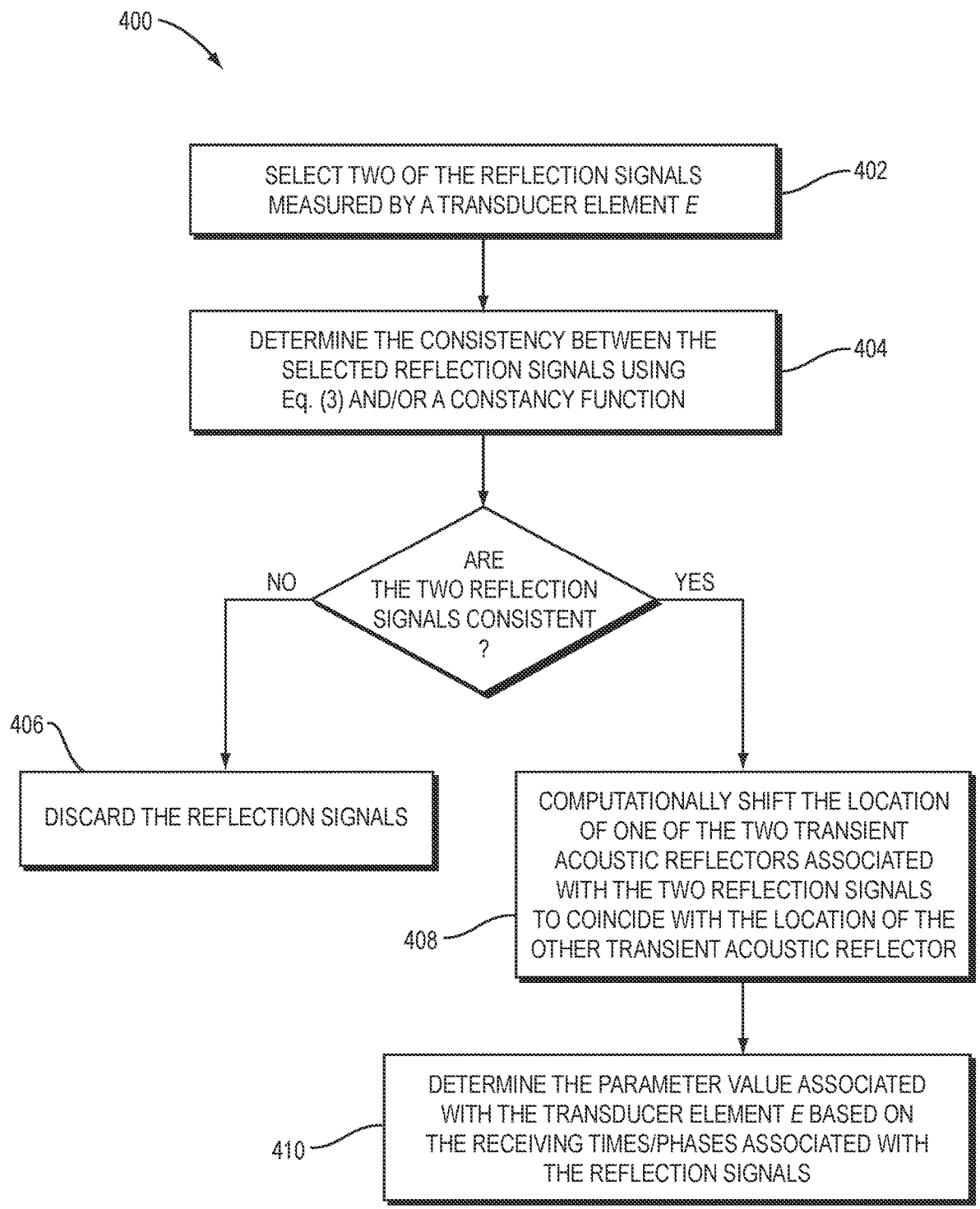
FIG. 4A is a flow chart illustrating a signal-selection approach for selecting the reflection signals in accordance with various embodiments.
Figure 4B:
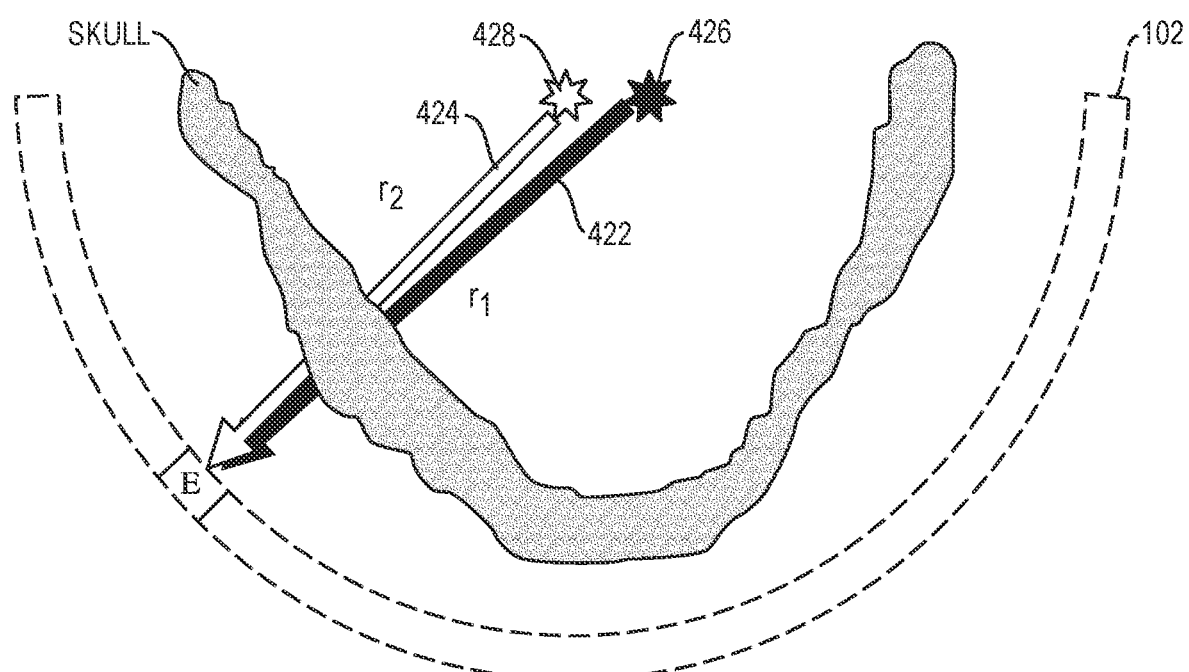
FIG. 4B depicts reflections of ultrasound signals from the transient acoustic reflectors in accordance with various embodiments.

Thus, prior to analyzing the reflection signals, a signal-selection approach is implemented to select the reflection signals (or difference signals) from single microbubble events to provide more accurate information about the focusing properties at the target region as well as to reduce the computational complexity of analyzing the reflection signals. In some embodiments, the signal-selection approach selects the reflection signals based on consistency therebetween. FIG. 4A depicts an exemplary signal-selection approach 400 for selecting the reflection signals in accordance herewith. In a first step 402, the controller 108 may select two of the reflection signals measured by a transducer element E. In a second step 404, the controller 108 may determine the consistency between the selected reflection signals using various approaches. For example, referring to FIG. 4B, assuming that two reflection signals 422, 424 originate with two microbubble events 426, 428, respectively, the travel times, $t_1$, $t_2$ for the respective reflection signals 422, 424 from the microbubble events 426, 428 to reach the transducer element F can be computed as:

$$t_1 = |\vec{r_1}|/c + \text{aberration}_1 \qquad \text{Eq. (1)}$$

$$t_2 = |\vec{r_2}|/c + \text{aberration}_2 \qquad \text{Eq. (2)}$$

where $|\vec{r_1}|$ and $|\vec{r_2}|$ denote the distances between the transducer element E and the microbubble events 426, 428, respectively; c denotes the speed of sound in the intervening tissue located between the transducer element E and the microbubble events; and aberration$_1$ and aberration$_2$ denote the aberrations caused by the intervening tissue located between the transducer element E and the microbubble events 426, 428, respectively.

In various embodiments, the microbubble events 426, 428 are selected based on a geometric criterion—e.g., they are spatially proximate (e.g., 2 mm apart); thus, if the reflection signals 422, 424 (or difference signals based thereon) from the microbubble events 426, 428 are consistent, the difference between the aberrations caused by the intervening tissue located between the transducer element E and the microbubble events 426, 428 can be ignored. As a result, in various embodiments, the reflection signals 422, 424 are considered to have sufficient consistency when the following equation is satisfied:

$$t_1 - t_2 \cong (|\vec{r_1}| - |\vec{r_2}|)/c \qquad \text{Eq. (3)}$$

Alternatively, the consistency between two reflection signals may be determined using a consistency function that takes into account measurements from more than one element. For example, the consistency function, $f(\vec{r'})$, may be defined as follows:

$$f(\vec{r'}) = \left| \frac{\sum_{\text{all elements}} W \times e^{-i\omega\left(t_1 - t_2 - \frac{dr}{c}\right)}}{\sum_{\text{all elements}} W} \right|, \qquad \text{Eq. (4)}$$

where W denotes a weighting factor; $\omega = 2\pi f$, where $f$ represents the frequency of the reflection signals; c is the average sound velocity in the target area; $\vec{r_i}$ the geometric location of the $i^{th}$ transient reflector; $|\vec{r_i}|$ and $|\vec{r_2}|$ are element-dependent variables that denote distances between one of the transducer elements measuring the two reflection signals and the transient acoustic reflectors associated with the two reflection signals, respectively; $t_i$ is the travel time of the $i^{th}$ transient reflector; $r' = \vec{r_1} - \vec{r_2}$; and $dr \equiv |\vec{r_1}| - |\vec{r_2}|$ for each transducer element. The consistency function, $f(\vec{r'})$, ins Eq. (4) may alternatively be expressed as.

$$f(\vec{r'}) = \left| \frac{\sum_{\text{all elements}} W \times e^{-i\left(\varphi_1 - \varphi_2 + \omega\left(\frac{dr}{c}\right)\right)}}{\sum_{\text{all elements}} W} \right|, \qquad \text{Eq. (5)}$$

where $\varphi_1$ and $\varphi_2$ denote the phases associated with the two reflection signals. In one embodiment, the two reflection signals are determined to be consistent or have sufficient consistency only when the value of the consistency function is maximized or exceeds a predetermined threshold (e.g., 0.5). For example, as described above, the reflection signals 422, 424 are considered consistent when $t_1-t_2 \cong (|\vec{r_1}|-|\vec{r_2}|)/c$; as a result, the consistency function, $f(\vec{r})$ defined in Eq. (4) has a value of one, which is larger than the predetermined threshold.

It should be noted that the consistency function provided above represents an example only; any other functions suitable for determining the relatedness of or consistency between two reflection signals can be used as (or in) the consistency function and are therefore are within the scope of the present invention.

Referring again to FIG. 4A, when the two reflection signals are determined to be inconsistent or have insufficient consistency, the reflection signals may be discarded (step 406). In contrast, when the two reflection signals are determined to be sufficiently consistent (e.g., when Eq. (3) is satisfied and/or when the value of the consistency function is maximized or exceeds the predetermined threshold), the two reflection signals can be further processed. Additionally, the controller 108 may discard all signals that are consistent with only a small (e.g., less than a pre-defined) number of other signals and process only the signals found to be consistent with more than the pre-defined number of signals. For example, referring to FIG. 4C, the controller 108 may computationally shift the location of one of the two transient acoustic reflectors (e.g., reflector 428) associated with the two reflection signals. It should be noted that shifting the reflector is generally done computationally rather than physically, i.e., data gathered from the reflector is computationally altered to simulate placement of the reflector in a different location. In one embodiment the transient acoustic reflector is shifted to coincide with the location of the other transient acoustic reflector (e.g., reflector 426) (step 408). As a result, the distance, $|\vec{r_2'}|$, between the shifted reflector 428 and the transducer element E can be represented as:

$$\delta r \equiv |\vec{r_1}| - |\vec{r_2}|$$

$$|\vec{r_2'}| = |\vec{r_2}| + \delta r$$

$$\frac{|\vec{r_2'}|}{c} = \frac{|\vec{r_2}|}{c} + \frac{\delta r}{c}$$

The travel time, $t_2'$, associated with the reflection signal from the shifted location of the reflector 428 can then be computed as:

$$t_2' = t_2 + \frac{\delta r}{c}$$

In one embodiment, the controller may search for $\vec{r_1}$ and/or $\vec{r_2}$ with which the signals consistency function is maximized. In various embodiments, the controller 108 can then determine the parameter value (e.g., amplitude and/or phase) associated with the transducer element F based on the travel times $t_1$ and $t_2'$ (step 410). Alternatively, since the phases $\varphi_1$ and $\varphi_2'$ associated respectively with the reflection signal 422 and shifted reflection signal 424 positively correlate to the travel times $t_1$ and $t_2'$, the controller 108 may determine the parameter value associated with the transducer element E based on the phases $\varphi_1$ and $\varphi_2'$. For example, the amplitude and/or phase associated with the transducer element E may be an average of the amplitudes and/or phases determined as described above based on the reflection signal 422 and the shifted reflection signal 424. Alternatively, the controller 108 may assign weighting factors to the travel times/phases associated with the shifted reflection signal 424 and the unshifted reflection signal 422, and determine the amplitude and/or phase associated with the transducer element E based on the weighted average thereof. In one embodiment, the weighting factors are assigned based on the amplitudes of the corresponding reflection signals and/or the consistency of the corresponding reflection signals with other reflection signals. For example, the reflection signal having a larger amplitude and/or higher consistency (e.g., a higher value of the consistency function) with other reflection signals may be assigned a larger weighting factor. Averaging the phase shifts associated with various reflection signals from different transient reflectors may also advantageously remove artifacts from the measured reflection signals.

Figure 4C:
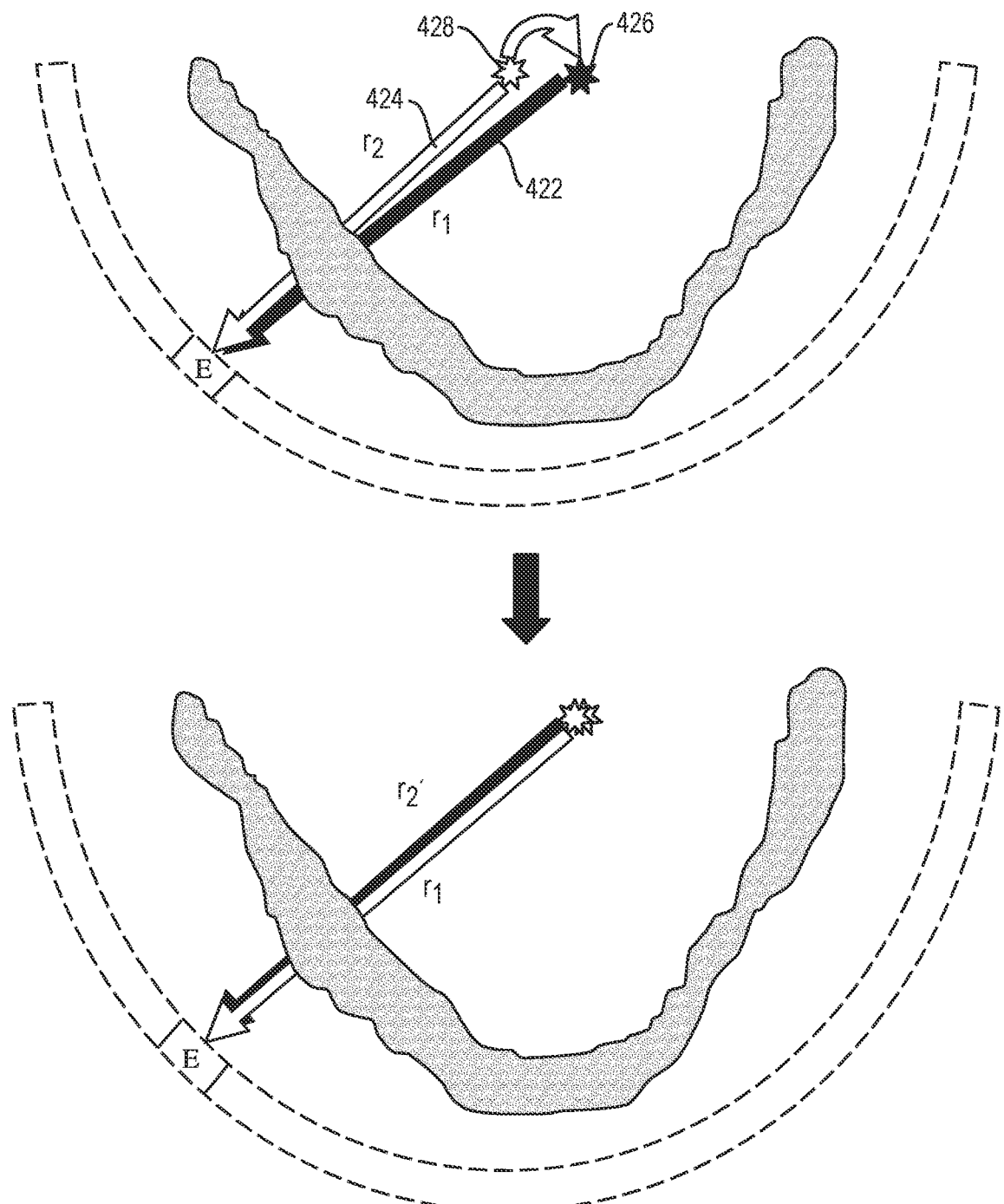
FIG. 4C depicts a computational shift of the location of a transient acoustic reflector to cause to coincide with the location of another transient acoustic reflector in accordance with various embodiments.

Although FIG. 4C depicts shifting one transient reflector to another transient reflector, it should be noted that step 408 can be performed to computationally shift all (or at least some) transient acoustic reflectors whose reflections are determined to have sufficient consistency such that they all coincide at a single location. The amplitude and/or phase associated with the transducer element E may then be computed as an average or a weighted average of the amplitudes and/or phases associated with the shifted reflection signals and/or the unshifted reflection signal at the coincident location.

Figure 4D:
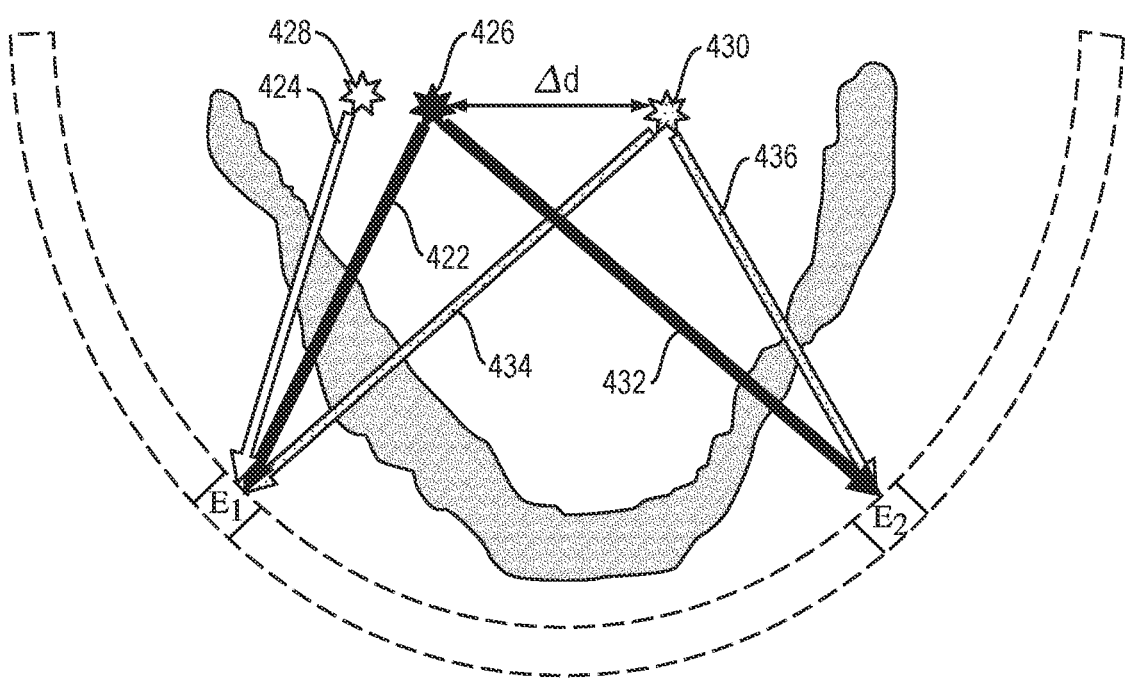
FIG. 4D depicts multiple reflection signals from multiple transient acoustic reflectors detected by multiple transducer elements in accordance with various embodiments.

In addition, although the signal-selection approach 400 described above determines consistency between two reflection signals, it should be noted that, in some embodiments, consistency among reflection signals from the same reflector received by multiple transducer elements can also be determined using the consistency function described above or any other suitable function. (It is also possible to measure consistency among signals from multiple reflectors received by the same transducer element.) For example, referring to FIG. 4D, reflection signals from three transient reflectors 426-430 may be detected by the transducer elements $E_1$ and $E_2$. The controller 108 may determine the consistency between the reflections 422, 424 from the respective reflectors 426, 428 detected by a transducer element (e.g., $E_1$ or $E_2$) using the approaches described above. In addition, the controller 108 may determine the consistency between more than two reflection signals (e.g., reflections 422, 432, 434, 436) from the reflectors 428, 430 detected by the transducer element $E_1$ and $E_2$ by comparing the reflections. For example, the respective travel times between two reflectors and a transducer element can be computed as set forth above based on the different distances $\delta r_1$ and $\delta r_2$ between the reflectors and the transducer element. Consistency can be computed in accordance, for example, with Eq. 4 or Eq. 5, and if the reflection signals 422, 432, 434, 436 have sufficient consistency, the reflections can be computationally shifted to coincide at a single location; subsequently, the configurations (e.g., amplitudes and/or phases) of the transducer elements Et and $E_2$ can be determined based on the amplitudes, travel times, and/or phases associated with the shifted and/or unshifted reflection signals.

In addition, although the signal-selection approach 400 described above determines consistency between two reflection signals, it should be noted that, in some embodiments, consistency between two reflection signals that capture more than one transient acoustic reflector can also be determined using a modification of the consistency function described above or any other suitable functions.

Figure 4E:
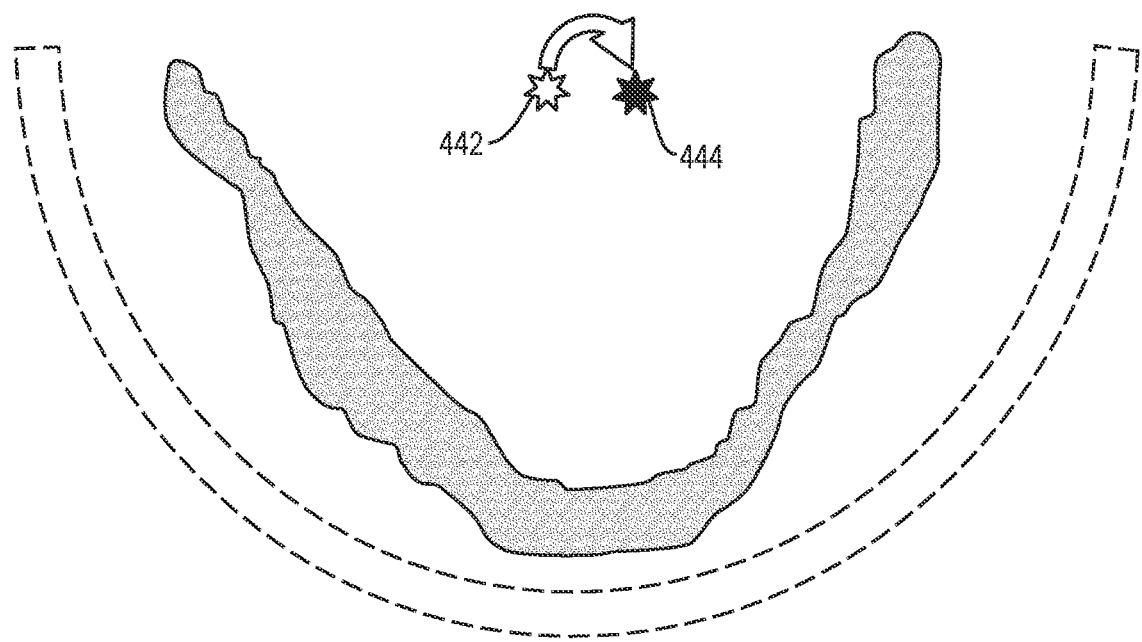
FIG. 4E depicts a computational shift of the coincident location associated with all (or at least some) of the transient acoustic reflectors to a sonication location determined using other approach(es) in accordance with various embodiments.

Referring to FIG. 4E, the coincident location 442 of all (or at least some) of the transient reflectors having sufficiently consistent reflection signals may be compared with a sonication location 444 determined using other approaches. For example, the imager 122 may be a CT device; by analyzing the acquired CT images of the target region and/or the non-target region surrounding the target region, the sonication location 444 of the ultrasound waves/pulses for treating the target region can be estimated. In one embodiment, the CT images are combined with a physical model to estimate the sonication location 444. The coincident location 442 of the transient reflectors may then be compared against the sonication location 444 estimated using the CT images and/or physical model. If there is a difference therebetween, the controller 108 may computationally shift the coincident location 442 to coincide with the estimated sonication location 444 and then computationally update the parameter value(s) of the transducer element(s) determined in step 410 so as to generate the ultrasound focus at the sonication location 444. The CT images and/or physical model may, in some embodiments, provide a more accurate estimate of the sonication location for treating the target, and the parameter value(s) of the transducer element(s) determined based on the transient reflectors located at the coincident location 442 may provide optimal focusing properties therein; in such cases, combining these estimates and parameter values (e.g., by shifting the coincident location 442 and updating the transducer parameter value(s)) may advantageously allow the ultrasound focus to be generated with enhanced locational accuracy for treating the target while retaining optimal focusing properties.

Figure 5:
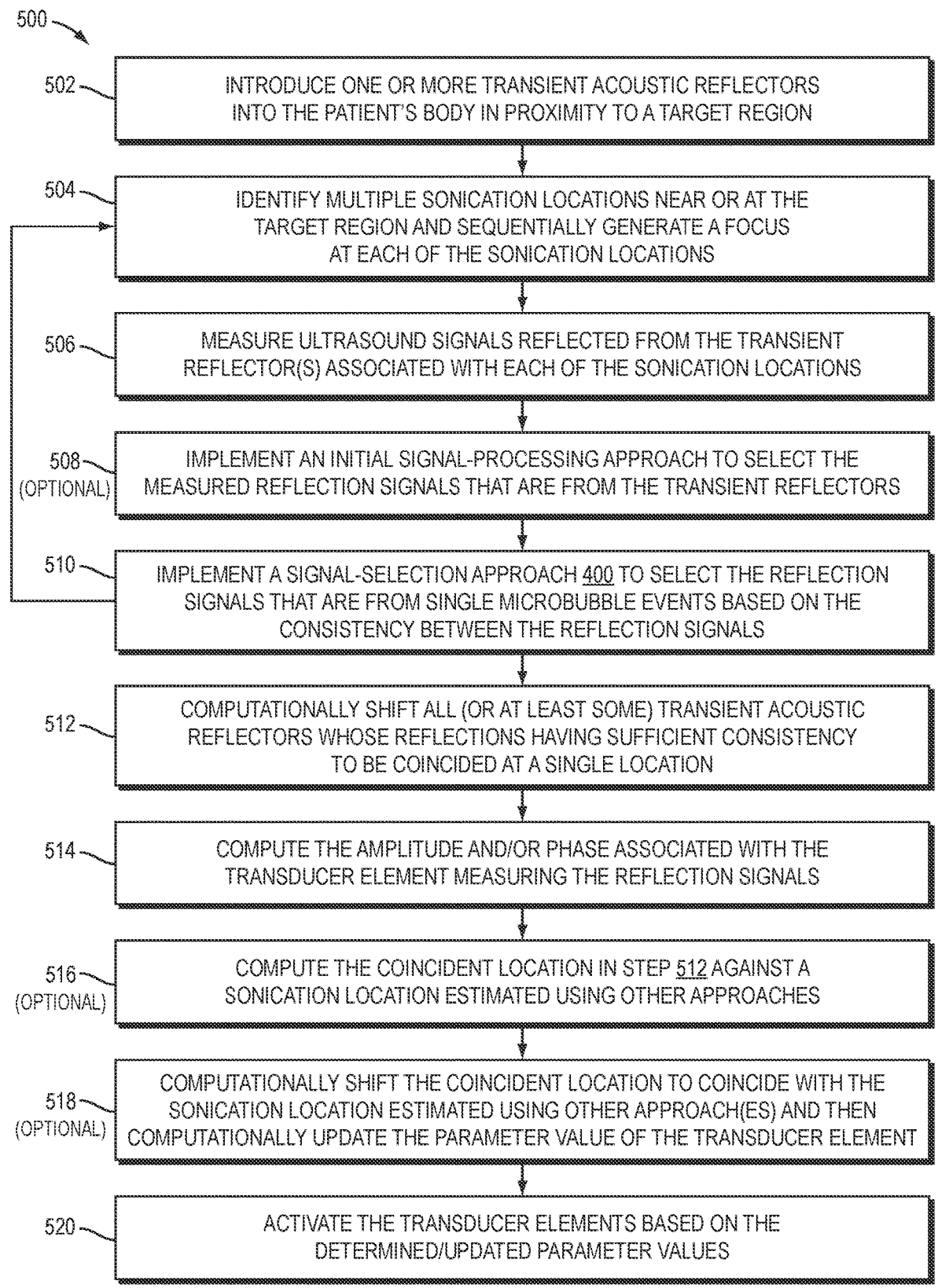
FIG. 5 is a flow chart illustrating an exemplary method for performing autofocusing of ultrasound waves/pulses using reflection signals from one or more transient acoustic reflectors in accordance with various embodiments.

FIG. 5 illustrates an exemplary approach 500 for performing autofocusing of ultrasound waves/pulses using reflection signals from one or more transient acoustic reflectors in accordance with various embodiments. In a first step 502, the transient acoustic reflector(s) (e.g., microbubbles) may be introduced into the patient's body in proximity to the target region. The reflector(s) may be introduced by an administration device 126 and/or generated by the acoustic energy transmitted from the transducer 102. In some embodiments, the controller 108 identifies multiple sonication locations near (e.g., less than 5 mm away) or at the target region; and the transient reflector(s) are introduced in proximity to (e.g., less than 5 mm away) each of the identified sonication locations. In a second step 504, the ultrasound transducer 102 may be activated to sequentially generate a focus at each of the identified sonication locations. In a third step 506, ultrasound signals reflected from the transient reflector(s) associated with each of the sonication locations may be measured by the transducer elements and/or the acoustic-signal detector 124. In an optional fourth step 508, an initial signal-processing approach 300/350 is implemented to select the measured reflection signals that are from the transient reflectors (as opposed to the background reflectors such as the skull). The initial signal-processing approach may be based on the comparison of the reflection signals between two consecutive measurements. For example, the two consecutively measured reflection signals may likely originate from the transient reflector(s) when there is a relatively significant change therebetween; this is because the transient reflector(s) generally evolves/dissipates during the period between two measurements, whereas the reflection signals from the persistent background reflectors during the period between two measurements are relatively invariant. Optionally, the difference signals may be computed by removing background signals from the measured signals, and these computed signals may used instead of the noisy measured signals in subsequent steps. For example, with renewed reference to FIG. 3B, signal 316 includes a background signal 314 and a reflection signal 324 from the transient reflector. Subtracting signal 314 from signal 316 removes the background signal therefrom, producing a difference signal in which the signal reflected from the transient reflector is dominant. Alternatively, the controller 108 may select another signal as the background image (e.g., a signal that is almost identical to one or more other signals or, instead, an average of multiple signals). Additionally or alternatively, the controller 108 may try more than one signal as the background signal and select the one that maximize the consistency function.

In a fifth step 510, the controller 108 may implement a signal-selection approach 400 to select the reflection signals from single microbubble events based on consistency between the reflection signals. In one embodiment, the reflection signals are considered to have sufficient consistency only when their associated parameters satisfy Eq. (3) and/or the value of the consistency function defined in, for example, Eq. (4) or (5) is maximized or exceeds a predetermined threshold. In a sixth step 512, the controller 108 may computationally shift all (or at least some) transient acoustic reflectors whose reflections have sufficient consistency to be coincided at a single location. In a seventh step 514, the amplitude and/or phase associated with the transducer element measuring the reflection signals may be computed as an average or a weighted average of the amplitudes and/or phases associated with the shifted reflection signals and/or the unshifted reflection signal at the coincident location so as to eliminate (or at least reduce) the artifacts in the measured reflections. In an optional eighth step 516, the coincident location in step 512 may be compared against a sonication location estimated using other approaches (e.g., CT images and/or physical model). If there is a deviation therebetween, the controller 108 may computationally shift the coincident location to coincide with the sonication location estimated using other approaches and then computationally update the parameter value of the transducer element determined in step 514 (step 518). Steps 506-518 may be performed sequentially or substantially simultaneously on an element-by-element basis for determining the parameter values (e.g., amplitudes and/or phases) of all (or at least some) elements of the ultrasound transducer. Thereafter, the transducer elements 104 may be activated based on their corresponding parameter values determined in step 514 or updated in step 518 so as to generate an ultrasound focus with optimal focusing properties at the target region (step 520).

In some embodiments, if the number of reflection signals that have been determined to have sufficient consistency in step 510 are below a predetermined threshold (e.g., 10, or in some embodiments, 20), the controller may repeat steps 504-508 before proceeding to step 512. This ensures that the amplitudes and/or phases associated with the transducer elements are determined based on a sufficient number of consistent reflection signals. Additionally or alternatively, in one embodiment, the controller 108 associates the reflection signals that have sufficient consistency with the corresponding sonication locations from which they are reflected; if the consistent reflection signals originate with a number of sonication locations below a predetermined threshold value (e.g., five sonication locations or, in some embodiments, 10 sonication locations), the controller 108 may repeat steps 504-508 without proceeding to step 512. Again, this approach can ensure that the consistent reflection signals originate with a sufficient number of different sonication locations so as to eliminate (or at least reduce) artifacts in the reflection signals.

One of ordinary skill in the art will understand that variations in the autofocusing approach described above are possible and are thus within the scope of the present invention. For example, it may not be necessary to activate a majority of the transducer elements 104 for performing autofocusing using the transient reflector(s) as described herein, and the number of transducer elements activated in each sonication of the sonication series may vary. For example, a fraction of the transducer elements 104 (e.g., 10%) may be selected to transmit and/or receive ultrasound waves in a first sonication associated with the first sonication location. The computed phase differences associated with the selected transducer elements may then be interpolated, extrapolated or processed using any suitable estimation approach to obtain the phase differences associated with unselected transducer elements. In the next sonication, a fraction of the previously unselected transducer elements may be used to repeat the autofocusing steps—i.e., transmitting ultrasound waves to the transient reflector(s) based on the interpolated (or extrapolated) phase differences and receiving reflections from the transient reflector. The selected transducer elements in the current sonication may or may not include the selected transducer elements in the precedent sonication(s) and the number of selected elements may be different in each sonication.

In general, functionality for performing autofocusing of ultrasound beams using reflection signals from one or more transient acoustic reflectors may be structured in one or more modules implemented in hardware, software, or a combination of both, whether integrated within a controller of the imager 122, an ultrasound system 100, and/or an administration system 126, or provided by a separate external controller or other computational entity or entities. Such functionality may include, for example, causing one or more transient acoustic reflectors to be introduced in the patient's body in proximity to a target region, identifying multiple sonication locations near or at the target region and sequentially generating a focus at each of the sonication locations, measuring ultrasound signals reflected from the transient reflector(s) associated with each of the sonication locations, comparing the measured reflection signals between two consecutive measurements to determine a difference therebetween (or a differential signal), computing an amplitude ratio between two consecutive differential signals, comparing the amplitude ratio to a predetermined threshold, selecting the reflection signals based on the comparison of the amplitude ratio, selecting a portion (e.g., a time window) of each of the measured reflection signals, determining the amplitude and/or phase associated with the selected portion of each reflection signal, determining a difference between the amplitudes and/or phases associated with the selected portions of the reflection signals in the two consecutive measurements, determining a noise level associated with the measured reflection signals, selecting the reflection signals based on the difference associated with the selected portions of the reflection signals and the noise level, selecting two of the reflection signals measured by a transducer element E, determining consistency between the selected reflection signals using Eq. (3) and/or a constancy function defined above, computationally shifting the location of one transient acoustic reflector to coincide with the location of another transient acoustic reflector, determining the parameter value associated with the transducer element E based on the travel times/phases associated with the reflection signals, comparing the coincident location against a sonication location estimated using other approach(es), computationally shifting the coincident location to coincide with the sonication location estimated using other approach(es) and then computationally updating the parameter value of the transducer element E, and activating the transducer element E based on the determined/updated parameter values, as described above.

In addition, the ultrasound controller, the imager and/or the administration system may include one or more modules implemented in hardware, software, or a combination thereof. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A system for focusing an ultrasound transducer, the system comprising:
   an ultrasound transducer comprising a plurality of transducer elements for providing sonications to at least one target region; and
   a controller configured to:
   (a) cause the transducer to generate a plurality of sonications to the at least one target region;
   (b) measure a reflection signal of each of the sonications off at least one transient acoustic reflector located in proximity to the at least one target region;
   (c) select the measured reflection signals based at least in part on: (i) an amplitude ratio of processed signals associated with sets of consecutive measurements, (ii) a distance between the at least one of the transducer elements and the at least one target region, (iii) a noise level associated with the reflection signals, or (iv) consistency therebetween; and
   (d) based at least in part on the selected reflection signals, adjust a parameter value associated with at least one of the transducer elements so as to improve an ultrasound focus at the target region.

2. The system of claim 1, wherein the controller is further configured to select reflection signals from two consecutive measurements and compare the selected reflection signals.

3. The system of claim 2, wherein the comparison corresponds to a first processed signal generated by subtracting a first background signal associated with a first set of the consecutive measurements from a first reflection signal associated with the first set the consecutive measurements.

4. The system of claim 3, wherein the controller is further configured to:
generate a second processed signal by subtracting a second background signal associated with a second set of the consecutive measurements from a second reflection signal associated with the second set the consecutive measurements; and
select the reflection signals based at least in part on an amplitude ratio of the first processed signal and the second processed signal.

5. The system of claim 4, wherein the controller is further configured to select the subtracted first processed signal upon determining that the ratio exceeds a predetermined threshold value.

6. The system of claim 1, wherein the controller is further configured to:
select at least a portion of each of the measured reflection signals; and
compare the selected portions of the reflection signals from two consecutive measurements.

7. The system of claim 6, wherein the controller is further configured to select the at least a portion based at least in part on a distance between the at least one of the transducer element and the at least one target region.

8. The system of claim 6, wherein the controller is further configured to:
determine at least one of an amplitude or a phase associated with the selected portion of each reflection signal; and
determine a difference between the amplitudes and/or phases associated with the selected portions of the reflection signals in the two consecutive measurements.

9. The system of claim 8, wherein the controller is further configured to:
determine a noise level associated with the reflection signals;
select the reflection signals based at least in part on the noise level and the difference associated with the selected portions of the reflection signals; and
adjust the parameter value associated with the at least one said transducer elements based at least in part on the difference upon determining that the difference of the amplitudes and/or phases associated with the selected portions of the reflection signals exceeds twice the noise level.

10. The system of claim 1, wherein the measured signals are pre-processed using at least one of a filter or IQ Demodulation.

11. The system of claim 1, wherein each of a plurality of the transient acoustic reflectors is located in proximity to one of a plurality of the target regions, the controller being further configured to:
sequentially generate the plurality of sonications to each of the transient acoustic reflectors and measure the reflection signals therefrom;
select the reflection signals associated with the plurality of sonications from the plurality of transient acoustic reflectors;
determine consistency among the reflection signals;
associate the reflection signals having sufficient consistency with the target regions; and
upon determining that the reflection signals having sufficient consistency are from a number of the target regions that is below a predetermined threshold value, repeat (a)-(c).

12. The system of claim 1, wherein the controller is further configured to determine the consistency between two reflection signals using a consistency function.

13. The system of claim 12, wherein the two reflection signals are determined to be consistent only when a value of the consistency function is maximized or exceeds a predetermined threshold.

14. The system of claim 12, wherein the consistency function satisfies at least one of the equations:

$$f(\vec{r'}) = \left| \frac{\sum_{all\ elements} W \times e^{-i\omega\left(t_1 - t_2 - \frac{dr}{c}\right)}}{\sum_{all\ elements} W} \right|,$$

$$f(\vec{r'}) = \left| \frac{\sum_{all\ elements} W \times e^{-i\left(\varphi_1 - \varphi_2 + \omega\left(\frac{dr}{c}\right)\right)}}{\sum_{all\ elements} W} \right|,$$

where W denotes a weighting factor; $\omega = 2\pi f$, $f$ represents the frequency associated with the two reflection signals; c is the average sound velocity in the target area; $\vec{r_i}$ is the geometrical location of the $i^{th}$ transient reflector; $r' = \vec{r_1} - \vec{r_2}$; $t_i$ is the travel time of the $i^{th}$ transient reflector; $\varphi_1$ and $\varphi_2$ denote the phases associated with the two reflection signals, and $dr \equiv |\vec{r_1}| - |\vec{r_2}|$, $|\vec{r_1}|$ and $|\vec{r_2}|$ are element-dependent variables that denote distances between one of the transducer elements measuring the two reflection signals and the transient acoustic reflectors associated with the two reflection signals, respectively.

15. The system of claim 14, wherein the controller is further configured to search for at least one of $\vec{r_1}$ or $\vec{r_2}$ to maximize the consistency function.

16. The system of claim 1, wherein the controller is further configured to determine the consistency between two of the reflection signals from two of the transient acoustic reflectors based at least in part on (i) at least one of travel times or receiving phases associated with the two of the reflection signals and (ii) locations associated with the two of the transient acoustic reflectors.

17. The system of claim 16, wherein the controller is further configured to:
computationally shift the location of a first one of the two transient acoustic reflectors to coincide with the location of a second one of the two transient acoustic reflectors;
computationally determine at least one of an updated travel time or an updated receiving phase associated with the reflection signal from the shifted location of the first one of the two transient acoustic reflectors; and
determine the parameter value associated with the at least one said transducer element based at least in part on (i) the updated travel time or the updated receiving phase and (ii) the travel time or the receiving phase of the reflection signal associated with the second one of the two transient acoustic reflectors.

18. The system of claim 17, wherein the controller is further configured to determine the parameter value associated with the at least one of the transducer elements based at least in part on an average of (i) the updated travel time or the updated receiving phase and (ii) the travel time or the receiving phase of the reflection signal associated with the second one of the two transient acoustic reflectors.

19. The system of claim 17, wherein the controller is further configured to assign a weighting factor to each of (i) the updated travel time or updated receiving phase and (ii) the travel time or receiving phase based on at least one of (i) an amplitude of the corresponding reflection signal or (ii) consistency of the corresponding reflection signal to other reflection signals, the parameter value associated with the at least one of the transducer elements being determined based at least in part on a weighted average of (i) the updated travel time or the updated receiving phase and (ii) the travel time or the receiving phase of the reflection signal associated with the second one of the two transient acoustic reflectors.

20. The system of claim 1, wherein the controller is further configured to determine the consistency between more than two reflection signals using a consistency function, said more than two reflection signals being measured by at least two different transducer elements.

21. The system of claim 12, wherein at least one of the reflection signals originates from at least two transient reflectors.

22. The system of claim 1, further comprising an imaging device for acquiring a plurality of images of the at least one target region and/or a non-target region surrounding the target region, the controller being further configured to:
estimate a location of the at least one target region based at least in part on the acquired images and a physical model; and
computationally update the parameter value associated with the at least one of the transducer elements so as to generate the ultrasound focus at the estimated target region.

23. The system of claim 1, further comprising an administration device for introducing the at least one transient acoustic reflector to the target.

24. The system of claim 1, wherein the controller is further configured to cause the transducer to generate acoustic energy for creating the at least one transient acoustic reflector.

* * * * *